US011401253B2

(12) United States Patent
Stierle et al.

(10) Patent No.: US 11,401,253 B2
(45) Date of Patent: Aug. 2, 2022

(54) 16-METHYL-OXACYCLOHEXADECAN-2-ONE AND 16-METHYL-AZACYCLOHEXADECAN-2-ONE DERIVATIVES AS ANTIMICROBIAL AGENTS

(71) Applicant: THE UNIVERSITY OF MONTANA, Missoula, MT (US)

(72) Inventors: Andrea Stierle, Missoula, MT (US); Donald Stierle, Missoula, MT (US); Nigel Priestley, Alberton, MT (US)

(73) Assignee: THE UNIVERSITY OF MONTANA, Missoula, MT (US)

( * ) Notice: Subject to any disclaimer, the term of this patent is extended or adjusted under 35 U.S.C. 154(b) by 134 days.

(21) Appl. No.: 16/495,312

(22) PCT Filed: Mar. 20, 2018

(86) PCT No.: PCT/US2018/023332
§ 371 (c)(1),
(2) Date: Sep. 18, 2019

(87) PCT Pub. No.: WO2018/175418
PCT Pub. Date: Sep. 27, 2018

(65) Prior Publication Data
US 2020/0017460 A1 Jan. 16, 2020

Related U.S. Application Data

(60) Provisional application No. 62/473,910, filed on Mar. 20, 2017.

(51) Int. Cl.
A61K 31/335 (2006.01)
C07D 313/00 (2006.01)
C07D 405/04 (2006.01)
C07D 491/044 (2006.01)
C07D 255/02 (2006.01)
A61P 31/04 (2006.01)
A61P 31/10 (2006.01)

(52) U.S. Cl.
CPC .......... C07D 313/00 (2013.01); A61P 31/04 (2018.01); C07D 405/04 (2013.01); C07D 491/044 (2013.01)

(58) Field of Classification Search
CPC .. A61K 31/335; C07D 313/00; C07D 405/04; C07D 491/044; C07D 255/02; A61P 31/04; A61P 31/10
USPC .......................................... 514/450; 549/346
See application file for complete search history.

(56) References Cited

PUBLICATIONS

Bao, J., X. Xu, X. Zhang and S. Qi, "A New Macrolide from a Marine-derived Fungus Aspergillus sp.", Natural Product Communications (2013), vol. 8(8), pp. 1127-1128. (Year: 2013).*

Bertrand et al., "De Novo Production of Metabolites by Fungal Co-culture of Trichophyton rubrum and Bionectria ochroleuca", Journal of Natural Products, vol. 76, pp. 1157-1165, 2013.
Bighnanshu et al., "First symmetric total synthesis of aspergillide D", Organic and Biomolecular Chemistry, vol. 15, pp. 1863-1871, 2017.
Boucher et al., "Bad bugs, no drugs: as antibiotic discovery stagnates, a public health crisis brews.", Infectious Disease Society of America, 37 pages, 2004.
Boucher et al., "Bad bugs, no drugs: no ESKAPE! An update from the Infectious Diseases Society of America", Clinical Infectious diseases: IDSA Report, 48, pp. 1-12, 2009.
Canova et al., "Synthesis and biological properties of macrolactam analogs of the natural product macrolide (-)-A26771B", Bioorganic & Medicinal Chemistry Letters, vol. 21, pp. 4768-4772, Jun. 2011.
Centers for Disease Control and Prevention, "Antibiotic/Antimicrobial Resistance (AR/AMR)", <http://www.cdc.gov/drugresistance/index.html>, webpage accessed Oct. 1, 2015.
Clark et al., "Caspase-3 Mediated Neuronal Death After Traumatic Brain Injury in Rats", Journal of Neurochemistry, 74, pp. 740-753, 2000.
Coffelt et al., "Inflammation lights the way to metastasis", Nature, vol. 507, pp. 48-49, 2014.
Comoglio et al., "Cancer: the matrix is now in control", Nature Medicine, vol. 11, No. 11, pp. 1156-1159, 2005.
Degenkolb et al., "Formation of New Lipoaminopeptides, Acremostatins A, B, and C, by Co-cultivation of Acremonium sp. Tbp-5 and Mycogone rosea DSM 12973", Biosci. Biotechnol. Biochem., vol. 66, No. 4, pp. 883-886, 2002.
Ekins et al., "Enhancing Hit Identification in Mycobacterium tuberculosis Drug Discovery Using Validated Dual-Event Bayesian Models PLOS ONE", 2013,8:5, e63240.
Franchi et al., "The Inflammasome: A Caspase-1 Activation Platform Regulating Immune Responses and Disease Pathogenesis", Nat. Immunol., vol. 10, No. 3, pp. 241-256, 2009.
Giddings et al., "Bioactive Compounds from Marine Extremophiles; In Springer Briefs in Microbiology; Extremophilic Bacteria", Tiquia-Arashiro, S. M.; Mormile, M.Eds.; Springer; Heidelberg, pp. 1-150, 2015.
Giddings et al., "Bioactive Compounds from Terrestrial Extremophiles; In Springer Briefs in Microbiology; Extremophilic Bacteria", Tiquia-Arashiro, S. M.; Mormile, M.Eds.; Springer; Heidelberg, pp. 1-90, 2015.
Hase et al., "Synthesis of the Macrolide Antibiotic A26771B Methyl Ester", Tetrahedron Letters, No. 28, pp. 2633-2636, 1979.
Hirota et al., "New Plant Growth Regulators, Cladospolide A and B, Macrolides Produced by Cladosporium cladosporioides", Agric. Biol. Chem., vol. 49, No. 3, pp. 731-735, 1985.

(Continued)

Primary Examiner — Joseph R Kosack
Assistant Examiner — Sagar Patel
(74) Attorney, Agent, or Firm — Michael Best & Friedrich LLP

(57) ABSTRACT 16-membered macrolide compounds inhibit growth of various microbial species and have utility in the treatment of systemic or topical microbial infections, including methicillin-resistant strains (Formula I).

19 Claims, 12 Drawing Sheets

(56) References Cited

PUBLICATIONS

Huang et al., "Two new cyclopeptides from the co-culture broth of two marine mangrove fungi and their antifungal activity", Pharmacogn. Mag., vol. 10, No. 40, pp. 410-414, 2014.

International Search Report and Written Opinion for Related Application No. PCT/US2018/023332 dated Aug. 17, 2018 (22 pages).

Jadulco et al., "New Macrolides and Furan Carboxylic Acid Derivative from the Sponge-Derived Fungus Cladosporium herbarum", J. Nat. Prod., 64, pp. 527-530, 2001.

Kakeya et al., "Studies on Prodrugs of Cephalosporings. I. Synthesis and Biological Properties of Glycyloxybenzoyloxymethyl and Glycylaminobenzoyloxymethyl Esters of 7-beta-[2-(2-Aminothiazol-4-yl)-(Z)-2-methoxyiminoacetamido]-3-methyl-3-cephem-4-carboxylic Acid", Chem Pharm Bull, vol. 32, No. 2, pp. 692-698, 1984.

Kobayashi et al., "An Efficient Synthesis of Antibiotic (-)-A26771B", J. Org. Chem., 65, pp. 612-615, 2000.

Li et al., "A new cyclopeptide with antifungal activity from the co-culture broth of two marine mangrove fungi", Natural Product Research, 28, pp. 616-621, 2014.

Liu et al., "Cytotoxic 14-Membered Macrolides from a Mangrove-Derived Endophytic Fungus, Pestalotiopsis microspora", Journal of Natural Products, 79, pp. 2332-2340, 2016.

Maag, "Prodrugs of Carboxylic Acids" Prodrugs: Challenges and Rewards Part 2, pp. 3-29, 2007.

Majumdar et al., "N-Alkyl-N-alkyloxycarbonylaminomethyl (NANAOCAM) prodrugs of carboxylic acid containing drugs", Bioorganic and Medicinal Chemistry Letters, vol. 17, pp. 1447-1450, 2007.

McIlwain et al., "Caspase Functions in Cell Death and Disease", Cold Spring Harbour Perspectives in Biology, 5; a008656, 2013.

Michael et al., "The isolation and structure elucidation of macrocyclic lactone antibiotic, A26771B", J Antibiot (Tokyo), vol. 30, No. 7, pp. 571-575, 1977.

Netzker et al., "Microbial communication leading to the activation of silent fungal secondary metabolite gene clusters", Frontiers in Microbiology, vol. 6, pp. 1-13, 2015.

Oh et al., "Induced Production of Emericellamides A nad B from the Marine-Derived Fungus Emericella sp in Competing Co-culture", Journal of Nature Prod., 70, pp. 515-520, 2007.

Radisky et al., "Rac1b and reactive oxygen species mediate MMP-3-induced EMT and genomic instability", Journal Nature, 436, pp. 123-127, 2005.

Ribeiro et al., "Aminocarbonyloxymethyl Ester Prodrugs of Flufenamic Acid and Diclofenac: Suppressing the Rearrangement Pathway in Aqueous Media", Arch. Pharm, Chem Life Sci, vol. 340, pp. 32-40, 2007.

Rodphaya et al., "New Macrolides from Penicillium Urticae Mutant S11R59", The Journal of Antibiotics, vol. 39, No. 5, pp. 629-635, 1986.

Schlosser et al., "Inhibition of caspase-1 induces cell death in pancreatic carcinoma cells and potentially modulates expression levels of bcl-2 family proteins", FEBS Letters, 491, pp. 104-108, 2001.

Sekiguchi et al., "Structure of Patulolide A, A New Macrolide from Penicillium Urticae Mutants", Tetrahedron Letters, vol. 26, No. 19, pp. 2341-2342, 1985.

Shigemori et al., "Sporiolide A and B, New Cytotoxic Twelve-Membered Marcolides from a Marine-Derived Fungus Cladosporium Species", Marine Drugs, 2, pp. 164-169, 2004.

Smith et al., "Novel Polyketide Metabolites from a Species of Marine Fungi", J. Nat. Prod., 63, pp. 142-145, 2000.

Stierle et al., "Berkeleyones and Related Meroterpenes from a Deep Water Acide Mine Waste Fungus That Inhibit the Production of Interleukin 1-Beta from Induced Inflammasomes", Journal of Natural Products, vol. 74, pp. 2273-2277, 2011.

Stierle et al., "Bioactive Secondary Metabolites from Acid Mine Waste Extremophiles" Natural Product Communications, vol. 9, No. 7, pp. 1037-1044, 2014.

Stierle et al., "Bioprospecting in the Berkeley Pit: The Use of Signal Transduction Enzyme Inhibition Assays to Isolate Bioactive Secondary Metabolites from the Extremophilic Fungi of an Acid Mine Waste Lake", Studies in Natural Products Chemistry, vol. 39, pp. 1-45, 2013.

Stierle et al., "Caspase-1 Inhibitors from an Extremophilic Fungus that Target Specific Leukemia Cell Lines", Journal of Natural Products, vol. 75, pp. 344-350, 2012.

Stierle et al., "Phomopsolides and Related Compounds from the Alga-associated Fungus, Penicillium clavigerum", Natural Product Communications, vol. 9, No. 7, pp. 87-90, 2014.

Stierle et al., "The Berkeleylactones, New Antibiotic Macrolides from a Berkeley Pit Fungal Co-Culture", 80: pp. 1150-1160, 2017.

Suzuki et al., "Interconversion among 16-Membered Macrolide Antibiotics Belonging to Leucomycin-Maridomycin Croup", Agric. Biolog. Chem., vol. 43, pp. 1331-1336, 1979.

Thiery et al., "Epithelial-Mesenchymal Transitions in Development and Disease", Cell, 139, pp. 871-890, 2009.

World Health Organization, "WHO Model List of Essential Medicines", <http://apps.who.int/iris/bitstream/10665/93142/1/EML_18_eng.pdf?ua=1>, 2013, webpage accessed Oct. 12, 2015, 47 pages.

Zhu et al., "Aspergicin, A New Antibacterial Alkaloid Produced by Mixed Fermentation of Two Marine-Derived Mangrove Epiphytic Fungi", Chemistry of Natural Compounds, vol. 47, pp. 767-769, 2011.

Zuck et al., "Induced Production of N-Formyl Alkaloids from Aspergillus fumigatus by Co-culture with Streptomyces peucetius", Journal of Natural Products, vol. 74, pp. 1653-1657, 2011.

European Patent Office Examination Report for Application No. 18717460.2 dated Nov. 17, 2020 (10 pages).

Jena et al., "First asymmetric total synthesis of aspergillide D", Organic & Biomolecular Chemistry, 2017, vol. 15, pp. 1863-1871.

* cited by examiner

BPL 76

BPL 88

BPL 81/A26771B

BPL 77

BPL 78

BPL 84

BPL 79

BPL 86

BPL 98

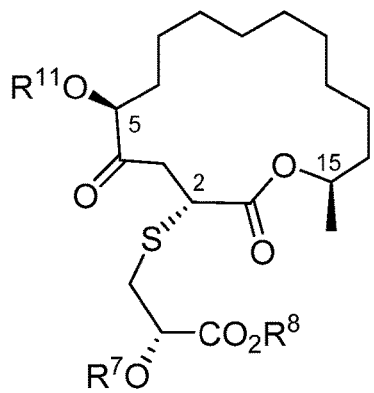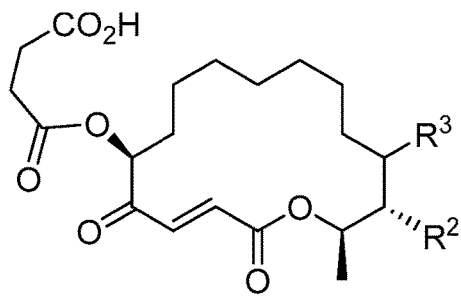

BPL76 $R^7, R^8, R^{11}$ = H
Methylated BPL76 $R^7, R^{11}$ = H, $R^8$ = $CH_3$
Acetylated BPL76 $R^7$ = H, $R^{11}$ = Ac, $R^8$ = $CH_3$
BPL88 $R^7, R^8$ = H, $R^{11}$ = $COCH_2CH_2CO_2H$

BPL81 $R^2$ = H, $R^3$ = H
BPL77 $R^2$ = OH, $R^3$ = H
BPL78 $R^2$ = H, $R^3$ = OH

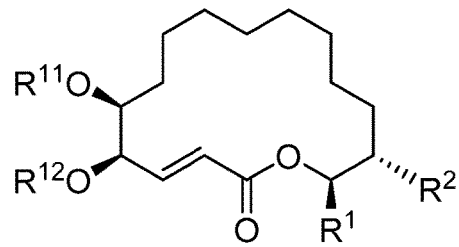

BPL84 $R^1$ = $CH_3$, $R^2, R^{12}$ = H, $R^{11}$ = $COCH_2CH_2CO_2H$
BPL79 $R^1$ = $CH_3$, $R^2$ = OH, $R^{11}, R^{12}$ = H
Acetylated BPL79 $R^1$ = $CH_3$, $R^2$ = OAc, $R^{11}, R^{12}$ = Ac
Chiral BPL79 $R^1$ = $CH_3$, $R^2$ = R or S OMTPA, $R^{11}, R^{12}$ = R or S MTPA
BPL86 $R^1$ = $CH_3$, $R^2$ = OH, $R^{11}$ = $COCH_2CH_2CO_2H$, $R^{12}$ = H
BPL 98 $R^1$ = $CH_2OH$, $R^2$ = H, $R^{11}$ = $COCH_2CH_2CO_2H$, $R^{12}$ = OH,

FIG. 2B

|  | Staphylococcus aureus (13709) | | Streptococcus pyogenes | | Candida glabrata | | Bacillus subtilis | | C. albicans | | B. anthracis | |
|---|---|---|---|---|---|---|---|---|---|---|---|---|
|  | µM | µg/mL | µM | µg/mL | µM | µg/mL | µM | µg/mL | µM | µg/mL | µM | µg/mL |
| BPL76 | 2 | 1 | 8 | 3 | 16 | 6 | 32 | 13 | 64 | 26 | 8 | 3 |
| BPL88 | 8 | 4 | 250 | 119 | 64 | 31 | 64 | 31 | >250 | >119 | 16 | 8 |
| BPL81 | 8 | 3 | 125 | 48 | 125 | 48 | 32 | 12 | 250 | 96 | 16 | 6 |
| BPL77 | 16 | 6 | 64 | 26 | 64 | 26 | 64 | 26 | 125 | 50 | 16 | 6 |
| BPL78 | 32 | 13 | 125 | 50 | >1000 | >400 | 250 | 100 | >1000 | >400 | 64 | 26 |
| BPL84 | 125 | 45 | >250 | >90 | >250 | >90 | >250 | >90 | >250 | >90 | >250 | >90 |
| BPL79 | 64 | 19 | 500 | 150 | >1000 | >300 | >1000 | >300 | >1000 | >300 | 250 | 75 |
| BPL86 | 64 | 24 | >125 | >50 | >125 | >50 | >125 | >50 | >125 | >50 | 64 | 24 |
| BPL98 | >250 | >100 | >250 | >100 | >250 | >100 | >250 | >100 | >250 | >100 | >250 | >100 |

FIG. 5

| CAIRD Isolate# | Description | BPL76 | BPL81 | Linezolid | Vancomycin | Erythromycin | Clindamycin | Levofloxacin | Doxycycline | Cefazolin |
|---|---|---|---|---|---|---|---|---|---|---|
| | | | | | | Antibiotics | | | | |
| | | | | | | MIC (µg/mL) | | | | |
| 116 | | 1 | 6 | 2 | 1 | >32 | >16 | >16 | 8 | 256 |
| 142 | USA100 HA-MRSA | 2 | 6 | 4 | 2 | >32 | >16 | 0.25 | 16 | 256 |
| 148 | | 1 | 6 | 2 | 0.5 | >32 | >16 | >16 | 0.25 | 256 |

FIG. 6

| | Staphylococcus aureus 13709 | Staphylococcus aureus Oxford | Staphylococcus aureus 25923 | Staphylococcus aureus 25923 10%HS | Staphylococcus aureus MRSAc | Streptococcus pyogenes | Enterococcus faecalis | Escherichia Coli | P.aer |
|---|---|---|---|---|---|---|---|---|---|
| BPL 81 | 2.00 | 2.00 | 4.00 | >32 | 2.00 | 16.00 | 16.00 | >32 | >32 |
| BPL 81 Butyl-succinate | 2.00 | 2.00 | 8.00 | >32 | 0.50 | 2.00 | 2.00 | >32 | >32 |
| BPL 81 Butyl est, 2 piperazine | 2.00 | 2.00 | 4.00 | >32 | 2.00 | 4.00 | 4.00 | >32 | >32 |
| BPL 81 5-OH | 1.00 | 1.00 | 2.00 | 32.00 | 2.00 | 2.00 | 2.00 | >32 | >32 |
| BPL 81 5-MeO | 1.00 | 1.00 | 1.00 | 16.00 | 0.50 | 2.00 | 2.00 | >64 | >64 |
| BPL 81 5-OAc | 0.50 | 1.00 | 1.00 | 16.00 | 0.50 | 2.00 | 4.00 | >64 | >64 |
| dh- BPL 81, 2-phenylthioether | 1.00 | 1.00 | 1.00 | 16.00 | 2.00 | 2.00 | >64 | >64 | >64 |
| dh- BPL 81, 2-phenylsulfonether | 1.00 | 1.00 | 1.00 | 32.00 | 2.00 | 4.00 | 4.00 | >64 | >64 |
| dh- BPL 81, 2-trifluoroethylthioether | 1.00 | 1.00 | 1.00 | 32.00 | 1.00 | 4.00 | 4.00 | >64 | >64 |
| BPL 81 lactam, a-5-MeO | 1.00 | 1.00 | 1.00 | 8.00 | 1.00 | 2.00 | 2.00 | >64 | - |
| BPL 81 lactam, b-5-MeO | 0.50 | 0.50 | 1.00 | 8.00 | 0.50 | 2.00 | 2.00 | >64 | - |
| BPL 81 Butyl est, 2-Phen-ox-ethylamine | >32 | >32 | >32 | >32 | >32 | >32 | >32 | >32 | >32 |
| BPL 81 Butyl est, 2,3-pyrazole | >64 | >64 | >64 | >64 | >64 | >64 | >64 | >64 | >64 |
| BPL 81 4,5-imidazole | 32.00 | 32.00 | 32.00 | >64 | 32.00 | 16.00 | 32.00 | >64 | >64 |
| dihydro- BPL 81, 5-MeO | >64 | >64 | >64 | >64 | >64 | >64 | >64 | >64 | >64 |
| BPL 81, 2-Me, 5-MeO | >64 | >64 | >64 | >64 | >64 | >64 | >64 | >64 | >64 |
| BPL 81, 2,3, Cycloprop, 5-MeO | 32.00 | 64.00 | 64.00 | >64 | >64 | 64 | 64.00 | >64 | >64 |
| BPL 81, 2,3-epoxide, 5-MeO | >64 | >64 | >64 | >64 | >64 | >64 | >64 | >64 | >64 |
| BPL 81, 2,3-epoxide, 5-MeO | >64 | >64 | >64 | >64 | >64 | >64 | >64 | >64 | >64 |

FIG. 7

16-METHYL-OXACYCLOHEXADECAN-2-ONE AND 16-METHYL-AZACYCLOHEXADECAN-2-ONE DERIVATIVES AS ANTIMICROBIAL AGENTS

CROSS-REFERENCE TO RELATED APPLICATION(S)

This application is a U.S. national stage entry of International Patent Application No. PCT/US2018/023332, filed on Mar. 20, 2018, which claims the benefit of U.S. Provisional Patent Application No. 62/473,910, filed on Mar. 20, 2017, the entire contents of each of which are fully incorporated herein by reference.

TECHNICAL FIELD

The invention relates to novel 16-membered macrolide compounds and pharmaceutically acceptable salts thereof, their use in the treatment of systemic or topical microbial infections, and methods of inhibiting microbial growth.

BACKGROUND

Macrolide antibiotics are important therapeutic agents and are considered to be one of the safest antibiotic treatments available. Macrolide compounds are characterized by the presence of a macrocyclic lactone ring, which can vary from 12 to 16 atoms, known as a macrolide ring, and usually one or more sugar chains is attached to the ring. Generally, macrolides inhibit protein synthesis in bacteria by reversibly binding to the P site of the 50S unit of the ribosome, thereby interrupting the growth of polypeptides.

Macrolide antibiotics such as erythromycin, clarithromycin, and azithromycin have been used widely to combat diseases caused by gram-positive pathogens and fastidious gram-negative pathogens. The popularity of this class of antibiotics is largely due to their spectrum of activity. Macrolide antibiotics generally share a similar range of activities against many strains of streptococci, staphylococci, clostridia, corynebacteria, *listeria, haemophilus* sp., *moxicella*, and *Neisseria meningitidis*. Clarithromycin and azithromycin are more active than erythromycin against several gram negative bacteria as well as *Mycoplasma* pneumonia, *Helicobacter pylori, Toxoplasma gondii*, cryptosporidia and several atypical mycobacteria.

Unfortunately, the widespread use and misuse of macrolides, and many other types of antibiotics, catalyzed the emergence of antimicrobial resistant strains. Among gram-positive bacteria, antibiotic resistant *Staphylococcus* and *Enterococcus* species pose the biggest threat. Certain gram-negative bacteria are becoming increasingly resistant to nearly all of the antibiotic drug options available, creating situations reminiscent of the pre-antibiotic era. Although overall antifungal resistance is still fairly low, many infections caused by the fungus *Candida* no longer respond to common antifungal medications. It is of critical importance to develop and provide new drugs with broad-spectrum activity, particularly against the ever increasing list of drug-resistant microbial species.

SUMMARY

The present invention relates to novel 16-membered macrolide compounds, their salts and pharmaceutical compositions and methods of use.

Compounds described herein may represent a new class of macrolide antibiotics useful for treating microbial infections and inhibiting microbial growth. Conventional macrolide antibiotics produced by bacterial species are polypropionate in nature. BPL 76 and related compounds are polyacetate derived. Conventional bacterially derived macrolides are active because of specific sugar moieties that interact within the ribosome to block bacterial protein synthesis. BPL 76 and analogs lack all sugar moieties and do not interfere with bacterial protein synthesis.

In one aspect, the invention provides a compound of formula (I), or pharmaceutically acceptable salt thereof,

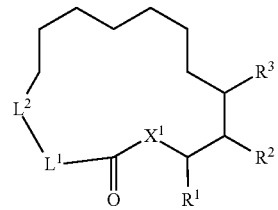

(I)

wherein
$X^1$ is O or NH;
$R^1$ is $C_{1-4}$alkyl, $C_{1-4}$haloalkyl, —$C_{1-3}$alkylene-OH, or —$C_{1-3}$alkylene-O$C_{1-4}$alkyl;
$R^2$ is hydrogen, OH, —O$C_{1-4}$alkyl, —OC(O)$C_{1-4}$alkyl, —OC(O)C(CF$_3$)(OCH$_3$)Ph, NH$_2$, —NH$C_{1-4}$alkyl, —N($C_{1-4}$alkyl)$_2$, —NHC(O)$C_{1-4}$alkyl, —N($C_{1-4}$alkyl)C(O)$C_{1-4}$alkyl, SH, —S$C_{1-4}$alkyl, or —SC(O)$C_{1-4}$alkyl;
$R^3$ is hydrogen, OH, —O$C_{1-4}$alkyl, —OC(O)$C_{1-4}$alkyl, NH$_2$, —NH$C_{1-4}$alkyl, —N($C_{1-4}$alkyl)$_2$, —NHC(O)$C_{1-4}$alkyl, —N($C_{1-4}$alkyl)C(O)$C_{1-4}$alkyl, SH, —S$C_{1-4}$alkyl, or —SC(O)$C_{1-4}$alkyl;
$L^1$ is

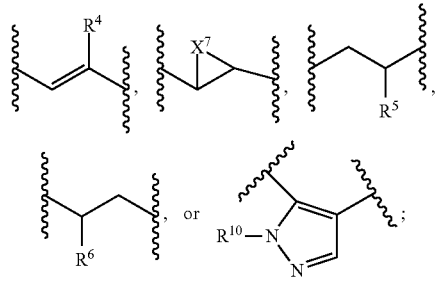

$X^7$ is H2 or O;
$R^4$ is hydrogen or methyl;
$R^5$ is hydrogen, —S$C_{1-4}$alkyl, —S$C_{1-4}$haloalkyl, or —S—$C_{1-3}$alkylene-CH($R^7$)—$X^2$;
$R^6$ is —S$C_{1-4}$alkyl, —S$C_{1-4}$haloalkyl, —S(O)$_n$-$G^1$, —N$R^9$—$C_{1-3}$alkylene-O-$G^1$, or $G^2$;
$R^7$ is hydrogen, $C_{1-4}$alkyl, OH, —O$C_{1-4}$alkyl, —OC(O)$C_{1-4}$alkyl, NH$_2$, —NH$C_{1-4}$alkyl, —N($C_{1-4}$alkyl)$_2$, —NHC(O)$C_{1-4}$alkyl, —N($C_{1-4}$alkyl)C(O)$C_{1-4}$alkyl, SH, —S$C_{1-4}$alkyl, or —SC(O)$C_{1-4}$alkyl;
$R^9$ is hydrogen, $C_{1-4}$alkyl, or —C(O)$C_{1-4}$alkyl;
$R^{10}$ is hydrogen or $C_{1-4}$alkyl;
$G^1$ is phenyl optionally substituted with 1-5 substituents independently selected from the group consisting of $C_{1-4}$alkyl, $C_{1-4}$haloalkyl, halo, cyano, OH, —O$C_{1-4}$alkyl, —CO$_2$$C_{1-4}$alkyl, and CO$_2$H;

n is 0, 1, or 2;

G² is a 4- to 8-membered monocyclic heterocycle containing a first nitrogen and optionally one additional heteroatom selected from nitrogen, oxygen, and sulfur, G² being attached at the first nitrogen and optionally substituted with 1-4 substituents independently selected from the group consisting of $C_{1-4}$alkyl, $C_{1-4}$haloalkyl, halo, cyano, OH, —$OC_{1-4}$alkyl, and oxo;

L² is

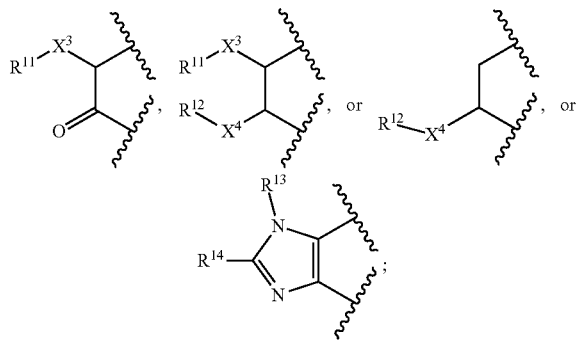

$X^3$ and $X^4$ are each independently O, S, NH, or $N(C_{1-4}alkyl)$;
$R^{11}$ is hydrogen, $C_{1-4}$alkyl, —$C(O)C_{1-4}$alkyl, —$C(O)C_{1-4}$alkylene-$X^5$, or —$C(O)C(CF_3)(OCH_3)Ph$;
$R^{12}$ is hydrogen, $C_{1-4}$alkyl, —$C(O)C_{1-4}$alkyl, —$C(O)C_{1-4}$alkylene-$X^6$, or —$C(O)C(CF_3)(OCH_3)Ph$;
$R^{13}$ is hydrogen or $C_{1-4}$alkyl;
$R^{14}$ is hydrogen or $C_{1-4}$alkyl; and
$X^2$, $X^5$, and $X^6$ are independently a carboxylic acid, a carboxylic acid bioisostere, or a prodrug thereof.

In another aspect, the invention provides a pharmaceutical composition comprising a compound of formula (I), or a pharmaceutically acceptable salt thereof, and a pharmaceutically acceptable carrier.

In another aspect, the invention provides a method of treating a microbial infection comprising administering to a subject infected with a microbe a therapeutically effective amount of a compound of formula (I), or a pharmaceutically acceptable salt or pharmaceutical composition thereof.

In another aspect, the invention provides a method of inhibiting a microbial growth comprising contacting a microbe with a therapeutically effective amount of a compound of formula (I), or a pharmaceutically acceptable salt or pharmaceutical composition thereof.

In another aspect, the invention provides a compound of formula (I), or a pharmaceutically acceptable salt or pharmaceutical composition thereof, for use in the treatment of a microbial infection.

In another aspect, the invention provides a compound of formula (I), or a pharmaceutically acceptable salt or pharmaceutical composition thereof, for use in the inhibition of a microbial growth.

In another aspect, the invention provides the use of a compound of formula (I), or a pharmaceutically acceptable salt thereof, in the manufacture of a medicament for the treatment of a microbial infection.

In another aspect, the invention provides the use of a compound of formula (I), or a pharmaceutically acceptable salt thereof, in the manufacture of a medicament for the inhibition of a microbial growth.

BRIEF DESCRIPTION OF THE DRAWINGS

FIG. 2B shows representative structures for the manufactured macrolides and select derivatives.

FIG. 5 shows the antibiotic testing data of macrolides.

FIG. 6 shows the comparison of antibiotic activity of BPL 76 and BPL 81 and several known antibiotics against methicillin-resistant strains of *S. aureus*. All antibiotic data for berkeleylactones was generated at University of Montana. Antibiotic data for linezolid, vancomycin, erythromycin, clindamycin, levofloxacin, doxycycline, and cefazolin was also generated at University of Montana.

FIG. 7 shows the antibiotic testing data of macrolides.

DETAILED DESCRIPTION

1. Definitions

Figure 1A:
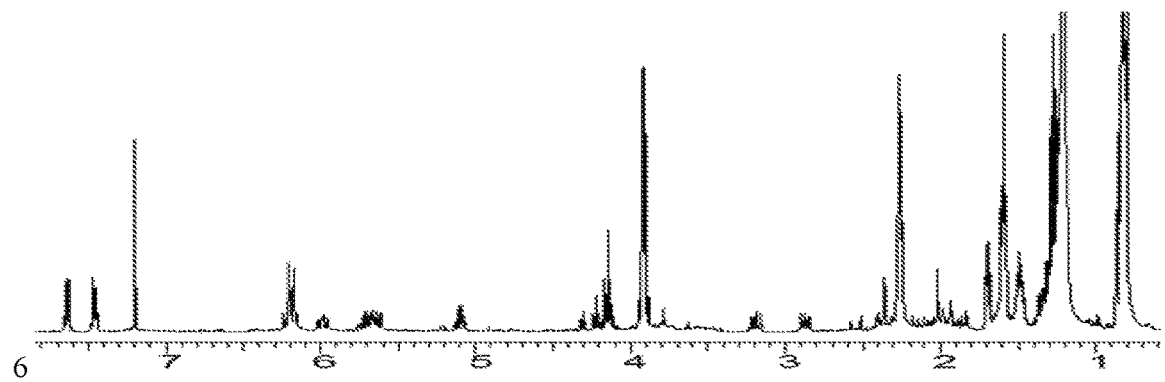
FIG. 1A shows the ¹H NMR spectra of chloroform extracts of an axenic culture of *Penicillium fuscum*.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample, or administration to a subject. Contacting encompasses administration to a solution, cell, tissue, mammal, subject, patient, or human. Further, contacting a cell includes adding an agent to a cell culture.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

As described herein, compounds of the invention can optionally be substituted with one or more substituents, such as are illustrated generally above, or as exemplified by particular classes, subclasses, and species of the invention. As described herein, the variables in formula I encompass specific groups, such as, for example, alkyl and cycloalkyl.

As one of ordinary skill in the art will recognize, combinations of substituents envisioned by this invention are those combinations that result in the formation of stable or chemically feasible compounds.

The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl," or as used herein, means a divalent group derived from a straight or branched chain saturated hydrocarbon. Representative examples of alkylene/alkylenyl include, but are not limited to, —$CH_2$—, —$CH_2CH_2$—, —$CH_2CH_2CH_2$—, —$CH_2CH(CH_3)CH_2$—, and $CH_2CH(CH_3)CH(CH_3)CH_2$—.

The term "carboxylic acid bioisostere," as used herein, refers to a replacement for the carboxylic acid functional group described in Lassalas et al., J. Med. Chem. (2016) 59, 3183-3203 and Ballatore et al., ChemMedChem (2013) 8(3) 385-395, which are incorporated herein by reference, and a carboxylic amide (e.g., alkyl amide). For example, representative examples of carboxylic acid bioisosteres include, but are not limited to, hydroxamic acids, phosphonic and phosphinic acids, sulfonic and sulfinic acids, sulfonamides, acylsulfonamides, sulfonylureas, 2,2,2-trifluoroethan-1-ol, trifluoromethylketones, tetrazoles, oxadiazole or thiadiazole systems, thiazolidinedione, oxazolidinedione, oxadiazolidine-dione, 3-hydroxyisoxazole, 3-hydroxyisothiazole, substituted phenols, squaric acid, 3- and 4-hydroxyquinolin-2-ones, tetronic and tetramic acids, cyclopentane-1,3-diones, boronic acids, mercaptoazoles, and sulfonimidamides.

"Carboxylic acid prodrug," as used herein, refers to a replacement for a carboxylic acid group described in Maag, "Prodrugs of Carboxylic Acids," in Prodrugs: Challenges and Rewards, Part 2, pp. 3-29, Springer 2007, Ribeiro et al., Arch. Pharm. Chem. Life Sci. (2007) 340, 32-40, Majumdar and Sloan, Bioorg. Med. Chem. Lett. (2007), 17, 1447-1450, Kakeya et al., Chem. Pharm. Bull. (1984) 32(2), 692-698, which are incorporated herein by reference. Representative carboxylic acid prodrugs include esters (e.g., alkyl such as methyl, ethyl, isopropyl, or n-butyl, aryl, acyloxymethyl, alkyloxycarbonyloxymethyl, benzoyloxymethyl, (oxodioxolyl)methyl, aminocarbonyloxymethyl, and N-alkyl-N-alkyloxycarbonylaminomethyl (NANOCAM)).

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1, 1-dimethylethyl, and the like.

The term "monocyclic heterocycle", as used herein, means a four-, five-, six-, seven-, or eight-membered ring containing at least one heteroatom independently selected from the group consisting of O, N, and S. The four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl.

Terms such as "alkyl" and "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The above substituents may be abbreviated herein. For example, the abbreviations Me, Et, Ph and Bn represent methyl, ethyl, phenyl and benzyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

In accordance with a convention used in the art, the group:

is used in structural formulae herein to depict the bond that is the point of attachment of the moiety or substituent to the core or backbone structure.

2. Compounds

Compounds of the invention have formula (I), wherein $R^1$, $R^2$, $R^3$, $L^1$, $L^2$, and $X^1$ are as defined herein. In some embodiments of formula (I), $X^1$ is O or NH; $R^1$ is $C_{1-4}$alkyl, $C_{1-4}$haloalkyl, —$C_{1-3}$alkylene-OH, or —$C_{1-3}$alkylene-O$C_{1-4}$alkyl; $R^2$ is hydrogen, OH, —O$C_{1-4}$alkyl, —OC(O)$C_{1-4}$alkyl, —OC(O)C(CF$_3$)(OCH$_3$)Ph, NH$_2$, —NH$C_{1-4}$alkyl, —N($C_{1-4}$alkyl)$_2$, —NHC(O)$C_{1-4}$alkyl, —N($C_{1-4}$alkyl)C(O)$C_{1-4}$alkyl, SH, —S$C_{1-4}$alkyl, or —SC(O)$C_{1-4}$alkyl; $R^3$ is hydrogen, OH, —O$C_{1-4}$alkyl, —OC(O)$C_{1-4}$alkyl NH$_2$, —NH$C_{1-4}$alkyl, —N($C_{1-4}$alkyl)$_2$, —NHC(O)$C_{1-4}$alkyl, —N($C_{1-4}$alkyl)C(O)$C_{1-4}$alkyl, SH, —S$C_{1-4}$alkyl, or —SC(O)$C_{1-4}$alkyl; $L^1$ is

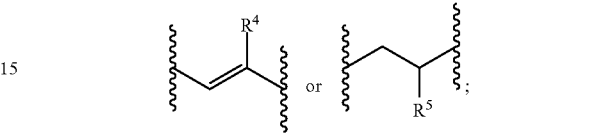

$R^4$ is hydrogen or methyl; $R^5$ is hydrogen, —S$C_{1-4}$alkyl, —S$C_{1-4}$haloalkyl, or —S—$C_{1-3}$alkylene-CH($R^7$)—$X^2$; $R^7$ is hydrogen, $C_{1-4}$alkyl, OH, —O$C_{1-4}$alkyl, —OC(O)$C_{1-4}$alkyl, NH$_2$, —NH$C_{1-4}$alkyl, —N($C_{1-4}$alkyl)$_2$, —NHC(O)$C_{1-4}$alkyl, —N($C_{1-4}$alkyl)C(O)$C_{1-4}$alkyl, SH, —S$C_{1-4}$alkyl, or —SC(O)$C_{1-4}$alkyl; $L^2$ is

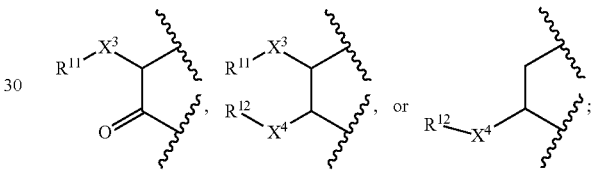

$X^3$ and $X^4$ are each independently O, S, NH, or N($C_{1-4}$alkyl); $R^{11}$ is hydrogen, $C_{1-4}$alkyl, —C(O)$C_{1-4}$alkyl, —C(O)$C_{1-4}$alkylene-$X^5$, or —C(O)C(CF$_3$)(OCH$_3$)Ph; $R^{12}$ is hydrogen, $C_{1-4}$alkyl, —C(O)$C_{1-4}$alkyl, —C(O)$C_{1-4}$alkylene-$X^6$, or —C(O)C(CF$_3$)(OCH$_3$)Ph; and $X^2$, $X^5$, and $X^6$ are independently a carboxylic acid, a carboxylic acid bioisostere, or a prodrug thereof; provided that a) one of $R^2$ and $R^3$ is not hydrogen, or b) $L^1$ is

$R^5$, where $R^5$ is —S$C_{1-4}$alkyl, —S$C_{1-4}$haloalkyl, or —S—$C_{1-3}$alkylene-CH($R^7$)—$X^2$; or c) $L^2$ is

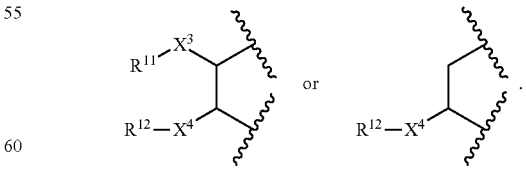

Accordingly, the compounds of these embodiments include compounds of formula (I), wherein $R^2$ is OH, —O$C_{1-4}$alkyl, —OC(O)$C_{1-4}$alkyl, —OC(O)C(CF$_3$)(OCH$_3$)Ph, NH$_2$, —NH$C_{1-4}$alkyl, —N($C_{1-4}$alkyl)$_2$, —NHC(O)$C_{1-4}$alkyl, —N($C_{1-4}$alkyl)C(O)$C_{1-4}$alkyl, SH, —S$C_{1-4}$alkyl, or —SC (O)C$_{1-4}$alkyl; and R$^1$, R$^3$, L$^1$, L$^2$, and X$^1$ are as defined herein. Also included are compounds of formula (I), wherein R$^3$ is OH, —OC$_{1-4}$alkyl, —OC(O)C$_{1-4}$alkyl NH$_2$, —NHC$_{1-4}$alkyl, —N(C$_{1-4}$alkyl)$_2$, —NHC(O)C$_{1-4}$alkyl, —N(C$_{1-4}$alkyl)C(O)C$_{1-4}$alkyl, SH, —SC$_{1-4}$alkyl, or —SC(O)C$_{1-4}$alkyl; and R$^1$, R$^2$, L, L$^2$, and X$^1$ are as defined herein. Also included are compounds of formula (I-a),

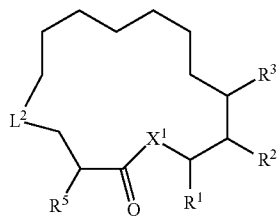
(I-a)

wherein R$^5$ is —SC$_{1-4}$alkyl, —SC$_{1-4}$haloalkyl, or —S—C$_{1-3}$alkylene-CH(R$^7$)—X$^2$; and R$^1$, R$^2$, R$^3$, L$^2$, and X$^1$ are as defined herein. Also included are compounds of formula (I-b) or (I-c)

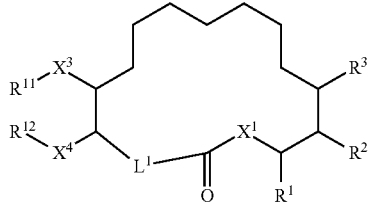
(I-b)

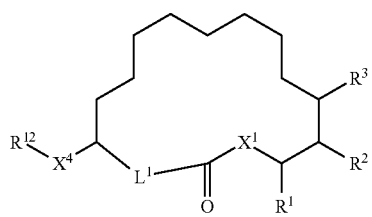
(I-c)

wherein R$^1$, R$^2$, R$^3$, R$^{11}$, R$^{12}$, L$^1$, X$^1$, X$^3$, and X$^4$ are as defined herein.

In some embodiments, L$^1$ is

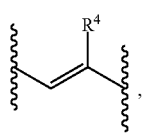

which connects to the adjacent moieties of formula (I) in the following orientation:

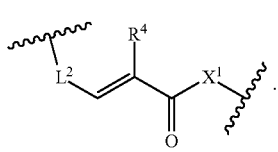

In some embodiments, L$^1$ is

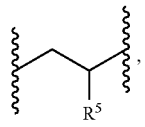

which connects to the adjacent moieties of formula (I) in the following orientation:

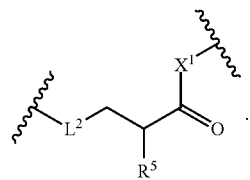

In some embodiments, L$^1$ has the following stereochemistry:

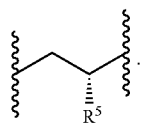

Included in the embodiments described herein are further embodiments wherein R$^5$ is —S—CH$_2$—CH(R$^7$)—X$^2$.

In some embodiments, L$^1$ is

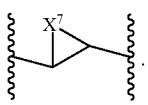

In some embodiments, L$^1$ is

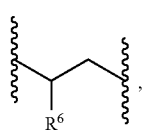

which connects to the adjacent moieties of formula (I) in the following orientation:

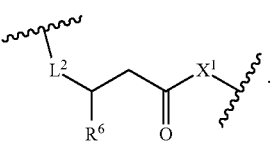

In some embodiments, R$^6$ is —SC$_{1-4}$alkyl, —SC$_{1-4}$haloalkyl, —S(O)$_n$-G$^1$, —NR$^9$—CH$_2$CH$_2$—O-G$^1$, or G$^2$; G$^1$ is phenyl; and G$^2$ is a 6- to 7-membered monocyclic heterocycle containing a first nitrogen and optionally one additional heteroatom selected from nitrogen, oxygen, and sulfur, G$^2$ being attached at the first nitrogen and optionally substituted with 1-4 substituents independently selected from the group consisting of $C_{1-4}$alkyl, $C_{1-4}$haloalkyl, halo, cyano, OH, —$OC_{1-4}$alkyl, and oxo.

In some embodiments, $L^1$ is,

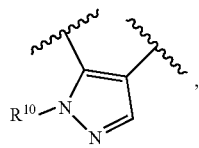

which connects to the adjacent moieties of formula (I) in the following orientation:

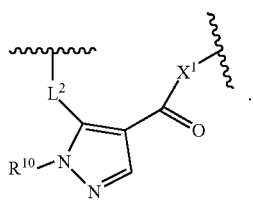

In some embodiments, $R^{10}$ is hydrogen.

In some embodiments, $L^2$ is

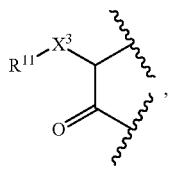

which connects to the adjacent moieties of formula (I) in the following orientation

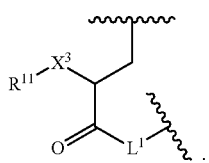

In some embodiments, $L^2$ has the following stereochemistry:

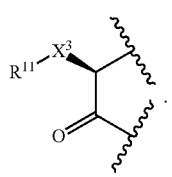

In some embodiments, $L^2$ is

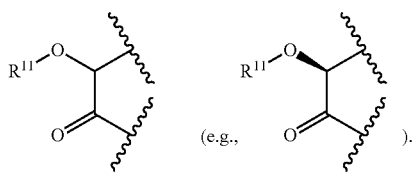 (e.g., ).

In these embodiments are further embodiments wherein $R^{11}$ is hydrogen, $CH_3$, —$C(O)CH_3$, —$C(O)CH_2CH_2$—$X^5$, or —$C(O)C(CF_3)(OCH_3)Ph$.

In some embodiments, $L^2$ is

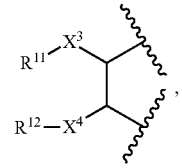

which connects to the adjacent moieties of formula (I) in the following orientation:

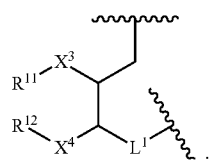

In some embodiments, $L^2$ has the following stereochemistry:

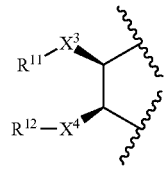

In some embodiments, $L^2$ is

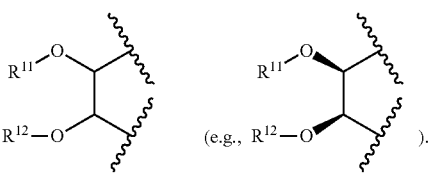 (e.g., ).

In these embodiments are further embodiments wherein $R^{11}$ is hydrogen, —$C(O)CH_3$, —$C(O)CH_2CH_2$—$X^5$, or —$C(O)C(CF_3)(OCH_3)Ph$; and $R^{12}$ is hydrogen, —$C(O)CH_3$, or —$C(O)C(CF_3)(OCH_3)Ph$. In still further embodiments, $R^{11}$ is hydrogen, —$C(O)C_{1-4}$alkyl, or —$C(O)C(CF_3)(OCH_3)Ph$; and $R^{12}$ is hydrogen, —$C(O)C_{1-4}$alkyl, —$C(O)C_{1-4}$alkylene-$X^6$, or —$C(O)C(CF_3)(OCH_3)Ph$. In yet further embodiments, $R^{11}$ is hydrogen, —$C(O)CH_3$, or —$C(O)C(CF_3)(OCH_3)Ph$; and $R^{12}$ is hydrogen, —$C(O)CH_3$, —$C(O)CH_2CH_2$—$X^6$, or —$C(O)C(CF_3)(OCH_3)Ph$.

In some embodiments, $L^2$ is

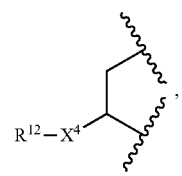

which connects to the adjacent moieties of formula (I) in the following orientation:

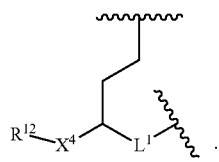

In some embodiments, $L^2$ has the following stereochemistry:

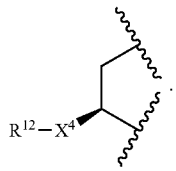

In some embodiments, $L^2$ is

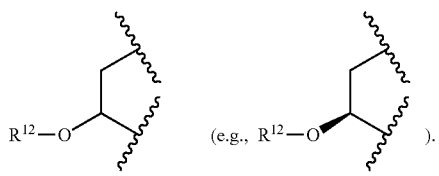

In these embodiments are further embodiments wherein $R^{12}$ is hydrogen.

In some embodiments, $L^2$ is

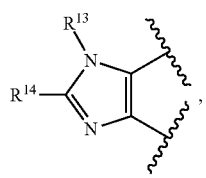

which connects to the adjacent moieties of formula (I) in the following orientation:

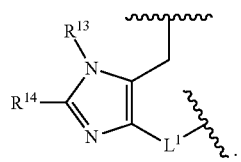

In these embodiments are further embodiments wherein $R^{13}$ is hydrogen and $R^{14}$ is $C_{1-4}$alkyl (e.g., methyl).

Included in the embodiments described herein are further embodiments wherein $R^1$ is $C_{1-4}$alkyl or —$C_{1-3}$alkylene-OH; and $R^2$ and $R^3$ are each hydrogen. In further embodiments, $R^1$ is methyl.

Included in the embodiments described herein are further embodiments wherein $R^1$ is $C_{1-4}$alkyl; $R^2$ is hydrogen; and $R^3$ is OH, —$OC_{1-4}$alkyl, or —$OC(O)C_{1-4}$alkyl. In further embodiments, $R^1$ is methyl. In further embodiments, $R^2$ is hydrogen; and $R^3$ is OH.

Included in the embodiments described herein are further embodiments wherein $R^1$ is $C_{1-4}$alkyl; $R^2$ is OH, —$OC_{1-4}$alkyl, —$OC(O)C_{1-4}$alkyl, or —$OC(O)C(CF_3)(OCH_3)Ph$; and $R^3$ is hydrogen. In further embodiments, $R^1$ is methyl. In further embodiments, $R^2$ is OH, —$OC(O)CH_3$, or —$OC(O)C(CF_3)(OCH_3)Ph$; and $R^3$ is hydrogen.

In any of the embodiments herein, $R^1$ may have the stereochemistry of formula (I-d).

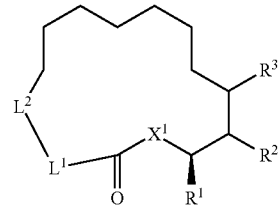

(I-d)

In any of the embodiments herein, $R^2$ may have the stereochemistry of formula (I-e).

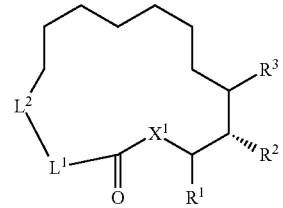

(I-e)

Included in the embodiments described herein are further embodiments wherein wherein $X^1$ is O.

Included in the embodiments described herein are further embodiments wherein $X^1$ is NH.

$X^2$, $X^5$, and $X^6$ are independently a carboxylic acid, a carboxylic acid bioisostere, or a prodrug thereof. In some embodiments, the carboxylic acid bioisostere is selected from the group consisting of a hydroxamic acid, phosphonic acid, phosphinic acid, sulfonic acid, sulfinic acid, sulfonamide, acylsulfonamide, sulfonylurea, 2,2,2-trifluoroethan-1-ol, trifluoromethylketone, tetrazole, oxadiazole, thiadiazole systems, thiazolidinedione, oxazolidinedione, oxadiazolidine-dione, 3-hydroxyisoxazole, 3-hydroxyisothiazole, substituted phenols, squaric acid, 3- and 4-hydroxyquinolin-2-ones, tetronic acid, tetramic acid, cyclopentane-1,3-dione, boronic acid, mercaptoazole, sulfonimidamide, and an N-alkylcarboxylic amide. In some embodiments, the carboxylic acid prodrug is selected from an alkyl ester (e.g., methyl, ethyl, isopropyl, or n-butyl), aryl ester, acyloxymethyl ester, alkyloxycarbonyloxymethyl ester, benzoyloxymethyl ester, (oxodioxolyl)methyl ester, aminocarbonyloxymethyl ester, and N-alkyl-N-alkyloxycarbonylaminomethyl (NANOCAM) ester.

In some embodiments, the compound of formula (I) is selected from the group consisting of
(S)-2-hydroxy-3-(((3R,6S,16R)-6-hydroxy-16-methyl-2,5-dioxooxacyclohexadecan-3-yl)thio)propanoic acid (BPL 76);
4-(((3R,6S,16R)-3-(((S)-2-carboxy-2-hydroxyethyl)thio)-16-methyl-2,5-dioxooxacyclohexadecan-6-yl)oxy)-4-oxobutanoic acid (BPL 88);
4-(((6S,16R,E)-16-methyl-2,5-dioxooxacyclohexadec-3-en-6-yl)oxy)-4-oxobutanoic acid (BPL 81);

4-(((6S,15S,16R,E)-15-hydroxy-16-methyl-2,5-dioxooxa-cyclohexadec-3-en-6-yl)oxy)-4-oxobutanoic acid (BPL 77);

4-(((6S,16R,E)-14-hydroxy-16-methyl-2,5-dioxooxacyclo-hexadec-3-en-6-yl)oxy)-4-oxobutanoic acid (BPL 78);

4-(((5R,6S,16R,E)-5-hydroxy-16-methyl-2-oxooxacyclo-hexadec-3-en-6-yl)oxy)-4-oxobutanoic acid (BPL 84);

(5R,6S,15 S,16R,E)-5,6,15-trihydroxy-16-methyloxacyclo-hexadec-3-en-2-one (BPL 79);

4-(((5R,6S,15 S,16R,E)-5,15-dihydroxy-16-methyl-2-oxooxacyclohexadec-3-en-6-yl)oxy)-4-oxobutanoic acid (BPL 86);

4-(((5R,6S,16S,E)-5-hydroxy-16-(hydroxymethyl)-2-oxooxacyclohexadec-3-en-6-yl)oxy)-4-oxobutanoic acid (BPL 98);

methyl (S)-2-hydroxy-3-(((3R,6S,16R)-6-hydroxy-16-methyl-2,5-dioxooxacyclohexadecan-3-yl)thio)propano-ate (Me-BPL 76);

methyl (S)-2-acetoxy-3-(((3R,6S,16R)-6-acetoxy-16-methyl-2,5-dioxooxacyclohexadecan-3-yl)thio)propano-ate (Ac-BPL 76);

(2R,3S,12S,13R,E)-2-methyl-16-oxooxacyclohexadec-14-ene-3,12,13-triyl triacetate (Ac BPL 79);

(2R,3S,12S,13R,E)-2-methyl-16-oxooxacyclohexadec-14-ene-3,12,13-triyl tris(3,3,3-trifluoro-2-methoxy-2-phe-nylpropanoate);

(5S,16R,E)-5-hydroxy-16-methyloxacyclohexadec-3-en-2-one (BPL 94);

(5R,6S,16R,E)-5,6-dihydroxy-16-methyloxacyclohexadec-3-en-2-one (BPL 95);

4-(((5R,6S,16R,E)-6-hydroxy-16-methyl-2-oxooxacyclo-hexadec-3-en-5-yl)oxy)-4-oxobutanoic acid (BPL 96);

tert-butyl ((6S,16R,E)-16-methyl-2,5-dioxooxacyclohexa-dec-3-en-6-yl) succinate;

(6S,16R,E)-6-methoxy-16-methyloxacyclohexadec-3-ene-2,5-dione;

(6S,16R,E)-16-methyl-2,5-dioxooxacyclohexadec-3-en-6-yl acetate;

(4R,14S)-14-methoxy-4-methyl-3-oxabicyclo[14.1.0]hepta-decane-2,15-dione;

(6S,16R)-6-hydroxy-16-methyl-4-((2,2,2-trifluoroethyl)thio)oxacyclohexadecane-2,5-dione;

(6S,16R,E)-6-methoxy-16-methylazacyclohexadec-3-ene-2,5-dione;

(6R,16R,E)-6-methoxy-16-methylazacyclohexadec-3-ene-2,5-dione;

(6S,16R,E)-6-methoxy-3,16-dimethyloxacyclohexadec-3-ene-2,5-dione;

tert-butyl ((6S,16R)-16-methyl-4-(4-methylpiperazin-1-yl)-2,5-dioxooxacyclohexadecan-6-yl) succinate;

tert-butyl ((6S,16R)-16-methyl-2,5-dioxo-4-(N-(2-phe-noxyethyl)acetamido)oxacyclohexadecan-6-yl) succi-nate;

(6S,16R)-6-methoxy-16-methyl-4-(phenylthio)oxacyclo-hexadecane-2,5-dione;

(6S,16R)-6-methoxy-16-methyl-4-(phenylsulfonyl)oxacy-clohexadecane-2,5-dione;

(6S,16R)-6-methoxy-16-methyloxacyclohexadecane-2,5-dione;

(4R,14S)-14-methoxy-4-methyl-3,17-dioxabicyclo[14.1.0] heptadecane-2,15-dione;

(6S,16R,E)-6-hydroxy-16-methyloxacyclohexadec-3-ene-2,5-dione;

(R,E)-2,8-dimethyl-8,9,10,11,12,13,14,15,16,17-deca-hydro-6H-112-[1]oxacyclohexadecino[5,6-d]imidazol-6-one;

tert-butyl ((6R,16S)-6-methyl-4,17-dioxo-6,7,8,9,10,11,12,13,14,15,16,17-dodecahydro-4H-112-[1]oxacyclohexa-decino[3,4-d]pyrazol-16-yl) succinate; or a pharmaceutically acceptable salt thereof.

Compounds in the foregoing list are named using Chem-BioDraw Ultra 14.0.0.117.

Certain compounds may exist in one or more particular geometric, optical, enantiomeric, diastereomeric, epimeric, atropic, stereoisomer, tautomeric, conformational, or ano-meric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "iso-meric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enan-tiomer, when used herein, refers to either of a pair of chemical compounds whose molecular structures have a mirror-image relationship to each other.

In one embodiment, a preparation of a compound dis-closed herein is enriched for an isomer of the compound having a selected stereochemistry, e.g., R or S, correspond-ing to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exem-plary selected stereocenters and exemplary stereoconfigura-tions thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereo-specific synthesis or by resolution. The compounds may, for example, be resolved into their component enantiomers or diastereomers by standard techniques, such as the formation of stereoisomeric pairs by salt formation with an optically active base, followed by fractional crystallization and regen-eration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Exemplary tautomeric forms include, for example, the following tautomeric pairs: keto/enol and imine/enamine.

Note that specifically included in the term "isomer" are compounds with one or more isotopic substitutions. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^2H$, can afford certain therapeutic advantages resulting from greater metabolic stability, for example, increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent. In some embodiments, in compounds of formula (I), any hydrogen atom may be deuterium.

A compound described herein can be in the form of a salt, e.g., a pharmaceutically acceptable salt. As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl (e.g., phenyl/substituted phenyl) sulfonate.

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C=O) is converted to a diether (R$_2$C(OR)$_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases (e.g., cyclic amines), as a nitroxide radical (>N-0<<).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—CH$_2$NHC(O)CH$_3$)

3. Methods of Use

The disclosed compounds and compositions may be used in various methods including methods of treatment and prevention of a microbial infection, or more particularly a microbial infectious disease or a disease or condition exacerbated or caused by a microbial infection comprising administering to a subject in need thereof a therapeutically effective amount of a compound of formula (I), or a pharmaceutically acceptable salt or pharmaceutical composition thereof.

The disclosed compounds and compositions may be used to inhibit microbial growth, for example, by contacting a therapeutically effective amount of the compound or composition with a microbe.

Also provided are uses of the compounds or compositions in the manufacture of a medicament for the treatment of a microbial infection or the inhibition of microbial growth.

The disclosed compounds and compositions may also be used as an anti-microbial agent in in vitro or ex vivo methods, e.g. in methods of cell culture or where the compound is used in the context of an abiotic or inanimate setting, e.g. to treat an inanimate surface to prevent, inhibit or reduce microbial colonization and/or growth, e.g. for decontamination, antiseptic, or sterilization purposes, or is applied to or contacted with a surface material, substrate, product, device or system susceptible to microbial growth, e.g. contamination such as in the preparation of a medical device of implant.

Compounds of the invention have several potential benefits as antibiotics for both bacterial and fungal species. BPL76 and analogs are as active against multi-drug resistant bacteria of certain genera as they are against antibiotic susceptible bacteria. These compounds have a unique mechanism of action among distantly related macrolides. Macrolide antibiotics that block bacterial protein synthesis generally promote resistance because of the interactions of their sugar moieties with the bacterial ribosome. Lacking such sugars, BPL76 will not induce bacterial antibiotic resistance in this same manner.

In some embodiments the microbe is a bacterium.

The bacterium may be a gram positive bacterial agent selected from the group comprising, but not limited to, *Staphylococcus* spp, *Streptococcus* spp, *Enterococcus* spp, *Leuconostoc* spp, *Corynebacterium* spp, *Arcanobacteria* spp, *Trueperella* spp, *Rhodococcus* spp, *Bacillus* spp, Anaerobic Cocci, Anaerobic Gram-Positive Nonsporulating Bacilli, *Actinomyces* spp, *Clostridium* spp, *Nocardia* spp, *Erysipelothrix* spp, *Listeria* spp, *Kytococcus* spp, *Mycoplasma* spp, *Ureaplasma* spp, and *Mycobacterium* spp.

Representative examples of *Staphylococcus* spp include *Staphylococcus epidermidis*, *Staphylococcus haemolyticus*, *Staphylococcus lugdunensis*, *Staphylococcus saprophyticus*, *Staphylococcus auricularis*, *Staphylococcus capitis*, *Staphylococcus caprae*, *Staphylococcus carnosus*, *Staphylococcus cohnii*, *Staphylococcus hominis*, *Staphylococcus pasteuri*, *Staphylococcus pettenkoferi*, *Staphylococcus pulvereri*, *Staphylococcus saccharolyticus*, *Staphylococcus simulans*, *Staphylococcus schleiferi*, *Staphylococcus warneri*, *Staphylococcus xylosus*, *Staphylococcus arlettae*, *Staphylococcus caseolyticus*, *Staphylococcus chromogenes*, *Staphylococcus condimenti*, *Staphylococcus delphini*, *Staphylococcus equorum*, *Staphylococcus felis*, *Staphylococcus fleurettii*, *Staphylococcus gallinarum*, *Staphylococcus hyicus*, *Staphylococcus intermedius*, *Staphylococcus kloosii*, *Staphylococcus lentus*, *Staphylococcus lutrae*, *Staphylococcus muscae*, *Staphylococcus nepalensis*, *Staphylococcus piscifermentans*, *Staphylococcus pseudintermedius*, *Staphylococcus sciuri*, *Staphylococcus simiae*, *Staphylococcus succinus*, and *Staphylococcus vitulinus*.

Representative examples of *Streptococcus* spp include *Streptococcus agalactiae*, *Streptococcus alactolyticus*, *Streptococcus anginosus*, *Streptococcus canis*, *Streptococcus constellatus*, *Streptococcus cricetus*, *Streptococcus cristatus*, *Streptococcus downed*, *Streptococcus dysgalactiae* subsp. *dysgalactiae*, *Streptococcus dysgalactiae* subsp. *equisimilis*, *Streptococcus equi* subsp. equi, *Streptococcus equi* subsp. *zooepidemicus*, *Streptococcus ferus*, *Streptococcus gallolyticus* subsp. *gallolyticus*, *Streptococcus gallolyticus* subsp. *pasteurianus*, *Streptococcus gordonii*, *Streptococcus hyointestinalis*, *Streptococcus hyovaginalis*, *Streptococcus infantarius*, *Streptococcus infantarius* subsp *infantarius*, *Streptococcus infantis*, *Streptococcus iniae*, *Streptococcus intermedius*, *Streptococcus lutetiensis*, *Streptococcus macaccae*, *Streptococcus mitis*, *Streptococcus mutans*, *Streptococcus oralis*, *Streptococcus orisratti*, *Streptococcus parasanguinis*, *Streptococcus peroris*, *Streptococcus pneumoniae*, *Streptococcus porcinus*, *Streptococcus pseudintermedius*, *Streptococcus pyogenes*, *Streptococcus ratti*, *Streptococcus salivarius*, *Streptococcus sanguinis*, *Streptococcus sobrinus*, *Streptococcus suis*, *Streptococcus thermophilus*, *Streptococcus vestibularis*, *Streptococci* (*Abiotrophia defectiva*, *Granulicatella adiacens*, *Granulicatella elegans*, and *Granulicatella para-adiacens*) and related species such as *Rothia mucilaginosa* (formerly *Stomatococcus mucilaginosus*) and *Pediococcus*.

Representative examples of *Enterococcus* spp include Enterococcusfaecalis, *Enterococcus faecium*, *Enterococcus gallinarum*, *Enterococcus durans*, *Enterococcus avium*, *Enterococcus raffinosus*, *Enterococcus pallens*, *Enterococcus gilvus*, *Enterococcus cecorum*, *Enterococcus malodoratus*, *Enterococcus italicus*, *Enterococcus sanguinicola*, *Enterococcus mundtii*, *Enterococcus casselifavus/flavescens*, *Enterococcus dispar*, *Enterococcus hirae*, *Enterococcus pseudoavium*, and *Enterococcus bovis*.

Representative examples of *Bacillus* spp include *Bacillus anthracis*, *Bacillus cereus*, *Bacillus circulans*, *Bacillus licheniformis*, *Bacillus megaterium*, *Bacillus pumilus*, *Bacillus sphaericus*, *Bacillus subtilis*, *Brevibacillus brevis*, *Brevibacillus laterosporus*, and *Paenibacillus alvei*.

Representative examples of *Mycobacterium* spp include *Mycobacterium abscessus*, *Mycobacterium arupense*, *Mycobacterium asiaticum*, *Mycobacterium aubagnense*, *Mycobacterium avium complex*, *Mycobacterium boletii*, *Mycobacterium bolletii*, *Mycobacterium branderi*, *Mycobacterium canettii*, *Mycobacterium caprae*, *Mycobacterium celatum*, *Mycobacterium chelonae*, *Mycobacterium chimaera*, *Mycobacterium colombiense*, *Mycobacterium conceptionense*, *Mycobacterium conspicuum*, *Mycobacterium elephantis*, *Mycobacterium farcinogenes*, *Mycobacterium florentinum*, *Mycobacteriumfortuitum* group, *Mycobacterium genavense*, *Mycobacterium goodii*, *Mycobacterium haemophilum*, *Mycobacterium heckeshomense*, *Mycobacterium heidelbergense*, *Mycobacterium houstonense*, *Mycobacterium immunogenum*, *Mycobacterium interjectum*, *Mycobacterium intracellulare*, *Mycobacterium senegalense*,

*Mycobacterium africanum, Mycobacterium avium* subsp *paratuberculosis, Mycobacterium kansasii, Mycobacterium lacus, Mycobacterium lentiflavum, Mycobacterium leprae, Mycobacterium lepraemurium, Mycobacterium mageritense, Mycobacterium malmoense, Mycobacterium marinum, Mycobacterium massiliense, Mycobacterium microti, Mycobacterium montefiorense* (eels), *Mycobacterium moracense, Mycobacterium mucogenicum, Mycobacterium nebraskense, Mycobacterium neoaurum, Mycobacterium novocastrense, Mycobacterium palustre, Mycobacterium parmense, Mycobacterium phlei, Mycobacterium phocaicum, Mycobacterium pinnipedii, Mycobacterium porcinum, Mycobacterium pseudoshottsii* (fish), *Mycobacterium pseudotuberculosis, Mycobacterium saskatchewanense, Mycobacterium scrofulaceum, Mycobacterium senuense, Mycobacterium septicum, Mycobacterium simiae, Mycobacterium smegmatis, Mycobacterium szulgai, Mycobacterium terrae/chromogenicum* complex, *Mycobacterium triplex, Mycobacterium tuberculosis, Mycobacterium tusciae, Mycobacterium ulcerans, Mycobacterium wolinskyi,* and *Mycobacterium xenopi.*

The bacterium may be a gram negative bacterial agent selected from the group comprising the following representative families: Acetobacteraceae, Aeromonadaceae, Alcaligenaceae, Anaplasmataceae, Armatimonadaceae, Bacteroidaceae, Bartonellaceae, Bdellovibrionaceae, Brachyspiraceae, Brucellaceae, Burkholderiaceae, Campylobacteraceae, Candidatus, Cardiobactenaceae, Chlamydiaceae, Chthonomonadaceae, Comamonadaceae, Coxiellaceae, Cytophagaceae, Desulfovibrionaceae, Enterobacteriaceae, Fimbriimonadaceae, Flavobacteriaceae, Francisellaceae, Fusobacteriaceae, Helicobacteraceae, Legionelaceae, Leptospiraceae, Leptotrichiaceae, Methylobacteriaceae, Moraxellaceae, Moritellaceae, Neisseriacae, Nitrosomonadaceae, Pasteurellaceae, Piscirickettsiaceae, Plesiomonadaceae, Polyangiaceae, Porphyromonadaceae, Prevotellaceae, Pseudomonadaceae, Rhizobiaceae, Rickettsiaceae, Shewanellaceae, Sphingomonadaceae, Spirillaceae, Spirochaetaceae, Succinivibrionaceae, Sutterellaoeae, Thermaceae, Thermotogaceae, Veillonellaceae, Vibrionaceae, Wolbachieae, and Xanthomonadaceae.

The bacteria causing the bacterial infection may be resistant to a conventional antibiotic used to treat the infection. The bacteria may be resistant to a compound selected from the group comprising: one or more of aminoglycosides; aminocyclitols; anti-MRSA cephalosporins; antipseudomonal penicillins+β-lactamase inhibitors; carbapenems; non-extended spectrum cephalosporins; 1st and 2nd generation cephalosporins; extended-spectrum cephalosporins; 3rd and 4th generation cephalosporins; cephamycins; fluoroquinolones; folate pathway inhibitors; fusidanes, glycylcyclines; lincosamides; macrolides and ketolides; monobactams; oxazolidinones; penicillins; penicillins+β-lactamase; phenicols; phosphonic acids; pleuromutilins; polymyxins; rifamycins; streptogramins; sulphonamides; tetracyclines.

In some embodiments the microbe is a fungus. The fungi may be unicellular, such as yeast, or multicellular, such as molds, mildews, and rusts. The fungi may reproduce sexually or asexually. The fungi may produce spores.

The fungus may be pathogenic in humans and include among others *Candida* spp. including *C. albicans, C. tropicalis, C. kejyr, C. krusei* and *C. galbrata; Aspergillus* spp. including *A. fumigatus* and *A. flavus; Cryptocccus neoformans; Blastomyces* spp. including *Blastomyces dermatitidis; Pneumocystis carinii; Coccidioides immitis; Basidiobolus ranarum; Conidiobolus* spp.; *Histoplasma capsulatum; Rhizopus* spp. including *R. oryzae* and *R. microsporus; Cunninghamella* spp.; *Rhizomucor* spp.; *Paracoccidioides brasiliensis; Pseudallescheria boydii; Rhinosporidium seeberi*; and *Sporothrix schenckii.*

The pathogenic fungus may be resistant to one or more other antifungal agents including; rapamycin or a rapalog, amphotericin B or analogs or derivatives or other polyene macrolide antibiotics, including, e.g., nystatin, candicidin, pimaricin and natamycin; flucytosine; griseofulvin; echinocandins or aureobasidins, inducing naturally occurring and semi-synthetic analogs; dihydrobenzo[a]napthacenequinones; nucleoside peptide antifungals including the polyoxins and nikkomycins; allylamines such as naftifine and other squalene epoxideuse inhibitors; and azoles, imidazoles and triazoles such as, e.g., clotrimazole, miconazole, ketoconazole, econazole, butoconazole, oxiconazole, terconazole, itraconazole or fluconazole and the like.

4. Pharmaceutical Compositions

In another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. In one embodiment, the pharmaceutical composition comprises a therapeutically effective amount of a compound of the present invention or a pharmaceutically acceptable salt thereof and one or more pharmaceutically acceptable carriers or vehicles.

In one aspect, provided is a pharmaceutical composition comprising a compound according to Formula (I), or a pharmaceutically acceptable salt thereof, and a pharmaceutically acceptable carrier.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease being treated.

Thus, the compounds and their pharmaceutically acceptable salts may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

The term "parenterally," as used herein, refers to modes of administration which include intravenous, intramuscular, intraperitoneal, intrasternal, subcutaneous and intraarticular injection and infusion.

Carriers for systemic administration may include one or more of diluents, lubricants, binders, disintegrants, colorants, flavors, sweeteners, antioxidants, preservatives, glidants, solvents, suspending agents, wetting agents, surfactants, emulsifying agents and dispersing agents, combinations thereof, and others. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, pills, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The pharmaceutical compositions of the present invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

Aerosol propellants are required where the pharmaceutical composition is to be delivered as an aerosol under significant pressure. Such propellants include, e.g., acceptable fluorochlorohydrocarbons such as dichlorodifluoromethane, dichlorotetrafluoroethane, and trichloromonofluoromethane; nitrogen; or a volatile hydrocarbon such as butane, propane, isobutane or mixtures thereof.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound is in the range of about 100 µg to about 250 mg per kilogram body weight of the subject per day.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

The present compounds, compositions, and methods may be administered as part of a therapeutic regimen along with other treatments appropriate for the particular injury or disease being treated.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

5. Compound Manufacture and Synthesis

Compounds of the invention may be prepared as illustrated in the following schemes and examples.

Abbreviations

Ac acetyl
BOC tert-butoxycarbonyl
Calcd calculated
$CDCl_3$ chloroform
DMAP 4-Dimethylaminopyridine
Et ethyl
Fmoc fluorenylmethyloxycarbonyl
h or hr hour
HATU 1-[Bis(dimethylamino)methylene]-1H-1,2,3-triazolo[4,5-b]pyridinium 3-oxide hexafluorophosphate
HMBC Heteronuclear multiple bond correlation
HOBt 1-hydroxybenzotriazole
HRESIMS high resolution electro-spray ionization mass spectrometry
Hz Hertz
IPA isopropyl alcohol
Me methyl
MeOH methanol
MTPA methoxy-(trifluoromethyl) phenylacetyl
NBS N-bromosuccinimide
OAc acetate
OMs mesylate
Ph phenyl
ppm parts per million
rt or r.t. room temperature
TFA trifluoroacetic acid
THF tetrahydrofuran Certain compounds were manufactured from a carefully timed co-culture fermentation of *Penicillium fuscum* and *P. camembertii/clavigerum*, two extremophilic fungi isolated from Berkeley Pit Lake. The compounds of the invention do not possess sugar moieties that have been considered essential to antibiotic activity, and do not block bacterial protein biosynthesis by binding to the 23S ribosomal RNA of the 50S subunit and interfering with the elongation of nascent peptide chains during translation. Some fungally derived macrolides are thought to require a double bond flanked by two carbonyl carbons for antibiotic activity. Surprisingly, the compounds of the invention display effective antibiotic activity against a broad spectrum of microbial agents without conforming to either of the structural-activity paradigms generally associated with the macrolide antibiotics.

Fungal Cultures.

The two fungal species *Penicillium fuscum* and *Penicillium camembertii/clavigerum* were isolated from a surface water sample taken from the Berkeley Pit, a former open-pit copper mine that is now filled with 40 billion gallons of acidic water, heavy metals and unique microscopic life forms. Each fungus was grown as an axenic culture in potato dextrose broth (shaken, room temperature, 200 rpm) for 7 days. At time of harvest, methanol was added to each culture, the mycelia were removed by gravity filtration and the filtrate was extracted with chloroform.

The two fungi were also co-cultured under controlled conditions. *P. fuscum* was grown in pure culture in potato dextrose broth (10×400 mL). After 24 h, an agar cube (8 $mm^3$) impregnated with *P. camembertii/clavigerum* mycelium was added to each flask and the resulting co-culture was shaken for 6 more days (200 rpm, room temperature). At time of harvest, methanol (50 mL/flask) was added, the mycelia were removed by gravity filtration and the broth was extracted with chloroform (3×2 L). The chloroform was removed in vacuo to yield 663 mg of crude extract. The crude extract was verified to be active in the MMP-3, caspase-1 and caspase-3 enzyme inhibition assays. Enzyme inhibitory activity was determined using specific BioMol enzyme inhibition assay kits for drug discovery as described in Stierle, A; Stierle, D. The Berkeleylactones, Antibiotic Macrolides from Fungal Coculture. J. Nat. Prod. 80, 4, 1150-1160.

Figure 1B:
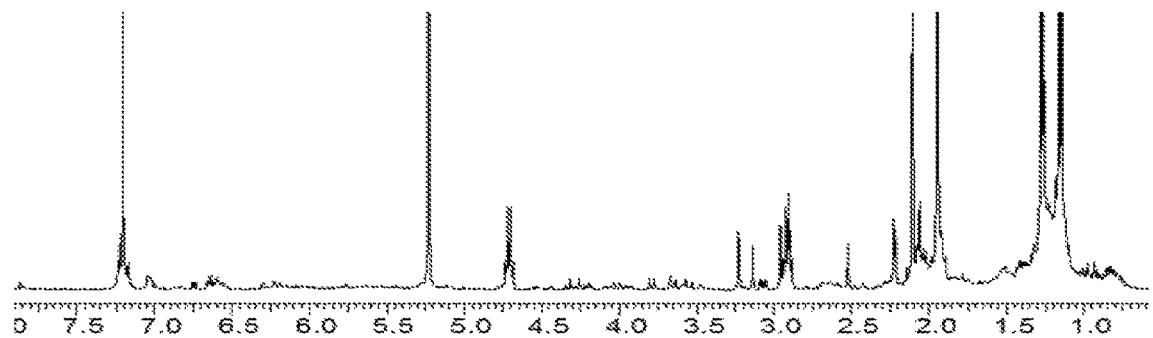
FIG. 1B shows the ¹H NMR spectra of chloroform extracts of an axenic culture of *Penicillium camembertii/calvigerum*.
Figure 1C:
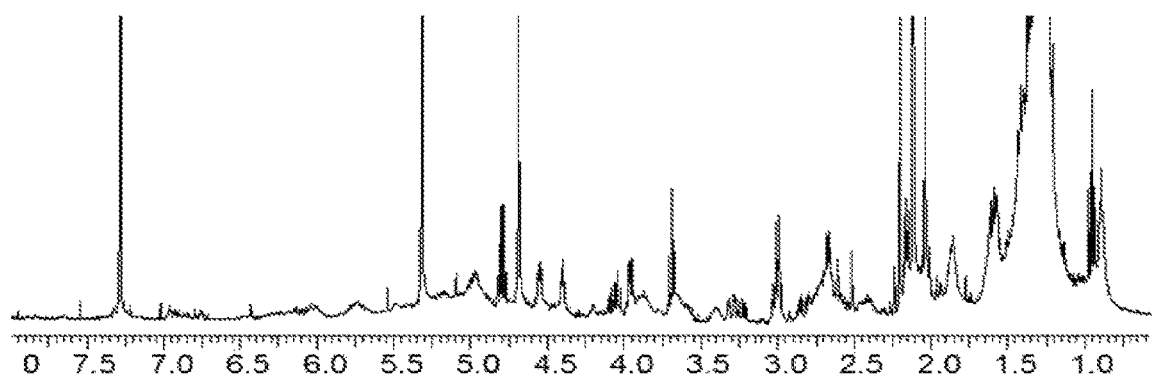
FIG. 1C shows the ¹H NMR spectra of chloroform extracts of a co-culture of *Penicillium fuscum* with *Penicillium camembertii/calvigerum*.

$^1$H NMR was performed on the chloroform extracts from both axenic cultures and the co-culture. The NMR spectra show that a selection of compounds (FIG. 2A) present in the co-culture (FIG. 1C) were not found in either pure culture (FIG. 1A-1B). The most abundant compounds in the chloroform extract of *P. camembertii/clavigerum* were citrinin and patulin, and in the chloroform extract of *P. fuscum* was asperfuran. In the co-culture, these compounds were part of a more complex mixture of metabolites.

A second co-culture experiment was run on a smaller scale (500 mL) under the same conditions described above but with the addition of methyl oleate to the broth (1.25 g/500 mL). Under these growth conditions the production of one of the metabolites, BPL 88, was enhanced from 0.6 mg/L to 4.0 mg/L.

Chemical and Structural Characterization.

Optical rotations were recorded on a Perkin-Elmer 241 MC Polarimeter using a 1.0 mL cell. IR spectra were recorded on a Perkin Elmer Spectrum One FT-IR spectrometer. 1D and 2D NMR spectra were recorded with a Bruker Avance 400 MHz instrument at 400 MHz for $^1$H NMR and 100 MHz for $^{13}$C NMR. Chemical shift values (δ) are given in parts per million (ppm), and the coupling constants (J) are in Hz. All of the chemical shifts were recorded with respect to the deuterated solvent shift (CDCl$_3$: $δ_H$ 7.24 for the proton resonance and $δ_C$ 77.0 for the carbon, MeOH-d$_4$: $δ_H$ 3.31 for the proton resonance and $δ_C$ 49.1 for the carbon). Both low and high resolution mass spectra were recorded on a Micromass LCT Premier XE mass spectrometer. X-ray structures were run on a Bruker D8 Venture instrument. All solvents used were spectral grade or distilled prior to use.

Purification of BPL Macrolides.

MMP-3 inhibition was used to direct the isolation of macrolides BPL 76, BPL 81, BPL 77, and BPL 79. $^1$H NMR spectral data was then used for chemotype-guided isolation of structurally related compounds that were weaker inhibitors of MMP-3, including BPL 88, BPL 78, BPL 84, BPL 86 and BPL 98.

The chloroform extract from the fungal co-culture was fractionated by flash silica gel column chromatography using a stepwise IPA-hexanes gradient system of increasing polarity starting with 5% IPA to 100% IPA (10%, 20%, 50% IPA), followed by 100% methanol. Fraction 1 (5% IPA-Hex) yielded pure citrinin (26.5 mg) and BPL81 (21.4 mg). Fraction 3 (20% IPA) was further resolved by HPLC using a semi-preparative silica gel column, Varian Dynamax Microsorb 100-5, with a gradient from 10% IPA-hexanes to 20% IPA-hexanes over 60 min to yield BPL 77 (6.0 mg) and BPL 84 (10.4 mg). Fraction 4 (50% IPA) was further resolved in a similar manner to yield BPL 76 (23.3 mg) and BPL 78 (5.8 mg). Fraction 5 (50% IPA) was also further resolved as described to yield BPL 88 (2.4 mg), BPL 79 (20.7 mg), BPL 86 (10.8 mg) and BPL 98 (1.7 mg).

Structure Determination of BPL 76.

NMR spectral data for BPL 76 was originally collected in both deuterated chloroform and deuterated methanol. Deuterated chloroform provided better resolution and peak dispersal, therefore it was used for the structure elucidation of BPL 76 (Table 1). The spectral data for all of the macrolides is directly compared in deuterated methanol. (Tables 2-5).

TABLE 1

$^1$H NMR, $^{13}$C NMR and HMBC data for BPL 76 in CDCl$_3$.

| position | $δ_C$, type | $δ_H$, mult (J in Hz) | HMBC correlations |
|---|---|---|---|
| 1 | 172.3, C | | 4.94, 4.01, 3.20, 2.80, |
| 2 | 41.3, CH | 4.01, t (7.0) | 3.27, 2.98, 3.20, 2.80 |
| 3 | 40.9, CH$_2$ | 3.20, dd (18.5, 7.0) 2.80, dd (18.5, 6.6) | 4.01 |
| 4 | 208.8, C | | 4.37, 4.01, 3.20, 2.80, 1.83 |
| 5 | 76.2, CH | 4.37, t (4.0) | 1.83 |

TABLE 1-continued $^1$H NMR, $^{13}$C NMR and HMBC data for BPL 76 in CDCl$_3$.

| position | $δ_C$, type | $δ_H$, mult (J in Hz) | HMBC correlations |
|---|---|---|---|
| 6 | 32.3, CH$_2$ | 1.83, m, 2H | 4.37 |
| 7 | 20.7, CH$_2$ | 1.38, m 0.97, m | 4.37, 1.83 |
| 8 | 26.0, CH$_2$ | 1.26 | 1.83 |
| 9 | 25.3, CH$_2$ | 1.26 | |
| 10 | 26.6, CH$_2$ | 1.26 | |
| 11 | 26.6, CH$_2$ | 1.26 | |
| 12 | 26.6, CH$_2$ | 1.26 | |
| 13 | 22.9, CH$_2$ | 1.32 | |
| 14 | 34.5, CH$_2$ | 1.55, m; 1.43, m | 4.94, 1.26 |
| 15 | 73.3, CH | 4.94, br dq (10.8, 6.2) | 1.55, 1.46, 1.26 |
| 16 | 19.8, CH$_3$ | 1.26, d (6.2) | |
| 1' | 174.9, C | | 4.53, 3.27, 2.98 |
| 2' | 70.4, CH | 4.53, dd (5.8, 3.7) | 3.27, 2.98 |
| 3' | 35.7, CH$_2$ | 3.27, dd (14.6, 3.7) 2.98, dd (14.6, 5.8) | 4.53, 4.01 |

BPL 76 had a molecular formula of C$_{19}$H$_{32}$O$_7$S with four sites of unsaturation, deduced from high-resolution electrospray ionization mass spectrometry (HRESIMS). The infrared spectrum showed a strong carbonyl absorbance at 1716 cm$^{-1}$ as well as abroad O—H stretch at 3443 cm$^{-1}$, typical of a carboxylic acid, and strong C—O stretching vibrations typical of an ester (1277, 1234, 1170 cm$^{-1}$). The $^{13}$C NMR data (CDCl$_3$) showed three carbonyl resonances ($δ_C$ 172.3, 174.9, and 208.8), also indicating the presence of a ketone ($δ_C$ 208.8). BPL 76 was readily methylated by diazomethane, yielding a methyl ester. Heteronuclear multiple bond correlation (HMBC) data of BPL 76 methyl ester showed correlations to the carbonyl carbon resonating at $δ_C$ 174.9, establishing it as the carboxylic acid C-1'. The $^{13}$C NMR data also provided evidence of three oxygen-bearing methines ($δ_C$ 76.2, 73.3 and 70.4). Acetylation of BPL 76 methyl ester yielded BPL 76 diacetate, indicating the presence of two hydroxy groups, which accommodated the remaining two oxygens. BPL 76 was determined to be monocyclic because the three carbonyls required three of the four sites of unsaturation.

Analysis of the $^1$H NMR data of BPL 76 (CDCl$_3$, Table 1) in conjunction with $^1$H-$^1$H COSY spectral data showed evidence of isolated spin system A: CH—CH$_2$ [H-2 ($δ_H$ 4.01), H$_2$-3 (δH 3.20, 2.80)]; and B: CH—CH$_2$ [H-2' (δH 4.53), H$_2$-3' (δH 3.27, 2.98)]. HMBC data showed long-range correlations (FIG. 2C) between the three protons of spin system A to both ketone C-4 ($δ_C$ 208.8) and to ester C-1 ($δ_C$ 172.3). The three protons of spin system B showed similar correlations to carboxylic acid C-1 ($δ_C$ 174.9). Three-bond coupling of methylene H-3' ($δ_H$ 3.27) to methine C-2 ($δ_C$ 41.3), and of methine H-2 ($δ_H$ 4.01) to C-3' ($δ_C$ 35.7) provided connectivity between spin-systems A and B (FIG. 1).

The position of the sulfide and the two hydroxy groups could also be determined using NMR spectral data and chemical shift arguments. In $^{13}$C NMR, a hydroxy group has a stronger deshielding effect on the chemical shift of adjacent carbons than a sulfide or methyl group (+41, +11, +9 ppm, respectively). An oxygen-bearing methine generally resonates downfield of 70 ppm, while a sulfur-bearing methine resonates between 30-40 ppm. In $^1$H NMR, there is a similar trend and the effects are additive. A proton attached to a sulfur-bearing carbon would resonate between 2.6 and 3.4 ppm. If the carbon were also attached to a carbonyl moiety, the proton would resonate around 4.00 ppm. These chemical shifts support the assignment of C-2 (spin system A) between ester C-1 ($\delta_C$ 172.3) and the sulfide moiety. They also support the assignment of C-3' (spin system B). The remaining hydroxy group is positioned at C-2' ($\delta_C$ 70.4). HMBC correlations between H-2 and C-3' and H-3' and C-2 as described above, provide further support for these assignments.

Spin system C begins at hydroxy-bearing methine C-5 ($\delta_C$ 76.2) and ends with methyl C-16: CHOH(CH$_2$)$_9$—CHOCH$_3$. The $^1$H-$^1$H COSY data showed $^3$J-coupling between H-5 ($\delta_H$ 4.37) and H$_2$-6 ($\delta_H$ 1.83, 2H). Methylene H$_2$-6 was further spin-coupled to H$_2$-7 ($\delta_H$ 1.38, 0.97), which was coupled to H$_2$-8 ($\delta_H$ 1.26). In the HMBC spectrum, H2-6 exhibited long-range coupling to ketone C-4, which provided connectivity to spin system A.

Figure 2A:
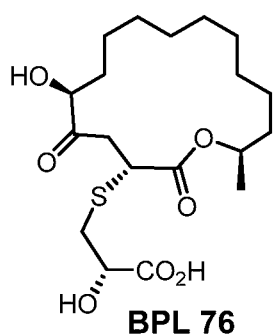
FIG. 2A shows representative structures for the macrolides manufactured from fungal co-cultures.
Figure 2A:
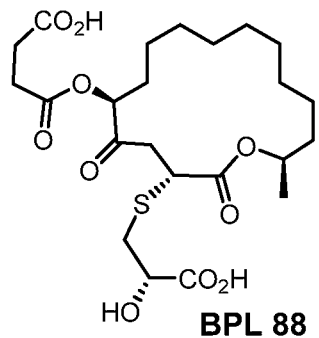
Figure 2A:
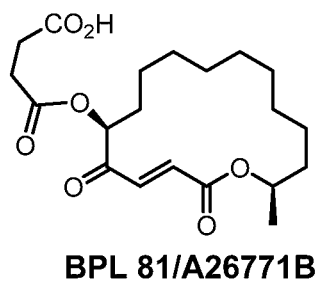
Figure 2A:
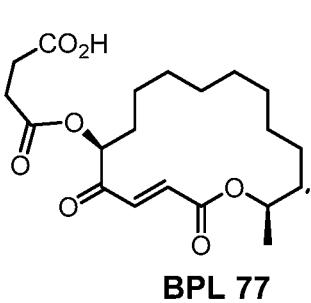
Figure 2A:
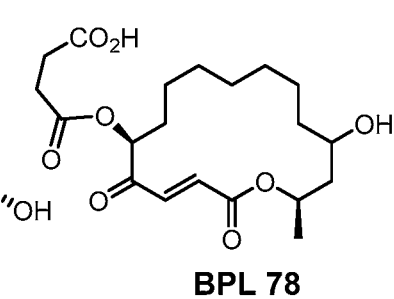
Figure 2A:
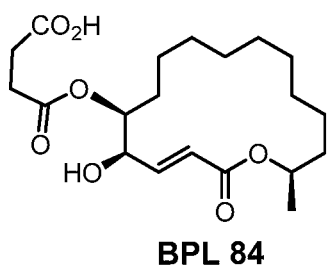
Figure 2A:
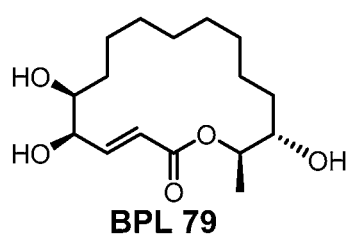
Figure 2A:
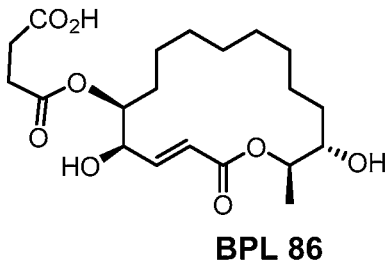
Figure 2A:
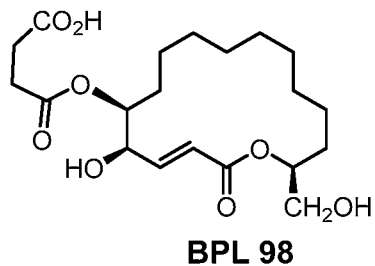

The terminus of spin system C could also be established using NMR spectral data. In the HMBC spectrum, oxygen-bearing methine H-15 ($\delta_H$ 4.94) showed long-range correlation to ester carbonyl C-1. This data not only confirmed that C-1 was the ester carbonyl but also provided connectivity between the terminus of spin system C and spin system A. COSY spectral data showed coupling between methine H-15 and to methyl H$_3$-16 ($\delta_H$ 1.26) and to methylene H$_2$-14 ($\delta_H$ 1.55, 1.43). C-8 through C-13 consisted of a methylene chain that could be connected to both ends of spin system C through $^1$H-$^1$H COSY and HMBC correlations. These data could be accommodated by BPL 76 as shown in FIG. 2A-2B.

BPL 76 characterization: colorless solid, [α]$^{25}_D$+0.5° (c 0.170, CHCl$_3$); IR (CHCl$_3$) $\nu_{max}$ 3443, 2932, 2860, 1716, 1277, 1234, 1170, 1094 cm$^{-1}$; $^1$H NMR see Tables 1 and 2; $^{13}$C NMR see Table 3: HRESIMS m/z [M–H]$^-$ 403.1799 (calcd for C$_{19}$H$_{31}$O$_7$S, 403.1791).

A single crystal X-ray diffraction study confirmed the structure (FIG. 2D) and allowed determination of the relative and absolute configurations of BPL 76. Colorless rods of BPL76 were obtained by diffusing pentane into a chloroform solution of BPL76. X-ray diffraction data for BPL76 was collected at 100 K using MoKα-radiation (λ=0.71073 Å). Data were corrected for absorption using SADABS area detector absorption correction program. Using Olex2, the structure was solved with the ShelXT structure solution program using Direct Methods and refined with the ShelXL refinement package using least squares minimization. All non-hydrogen atoms were refined with anisotropic thermal parameters. Hydrogen atoms attached to heteroatoms were found from the residual density maps and refined with isotropic thermal parameters. All other hydrogens atoms were refined in calculated positions using a ridged group model. The absolute structure was determined by refinement of the Flack Parameter, based on anomalous scattering, with a final Flack parameter of 0.00(2). All calculations and refinements were carried out using APEX2, SHELXTL, and Olex2 software. Crystallographic data for BPL76 have been deposited with the Cambridge Crystallographic Data Centre. The absolute configuration of BPL 76 (FIG. 2D) was determined and shown to be 2R, 5S,15R and 2'S.

Crystallographic Data for BPL76: C$_{19}$H$_{32}$O$_7$S, M=404.50, monoclinic, space group P2$_1$, a=10.6258(10), b=5.2403(5), c=18.8604(17), β=102.984(2), V=1023.34 (17), Z=2, T=100 K, μ(MoKα)=0.195 mm$^{-1}$, ρ$_{calcd}$=1.313 g ml$^{-1}$, 2θ$_{max}$=68.870, 44910 reflections collected, 8604 unique (R$_{int}$=0.0656, R$_{sigma}$=0.0528), R1=0.0470 (I>2σ(I)), wR2=0.1022 (all data), Flack Parameter=0.00(2), CCDC number; 1040078.

Structure Determination of BPL 88.

The molecular formula of BPL 88 was determined to be C$_{23}$H$_{36}$O$_{10}$S based on HRESIMS. BPL 88 had four more hydrogens, four more carbons, three more oxygens, and two more sites of unsaturation than BPL 76. In the infrared spectrum, the carbonyl region of BPL 88 showed overlapping absorbances between 1738-1716 cm$^{-1}$. The $^1$H NMR data of BPL 76 and BPL 88 in deuterated methanol (Table 2) were very similar except for the downfield shift of H-5 from $\delta_H$ 4.30 to $\delta_H$ 5.17 in compound BPL 88, and the addition of two 2H multiplets at ($\delta_H$ 2.66 and $\delta_H$ 2.60 ppm in BPL 88. The $^{13}$C NMR data of BPL 88 (Table 3) showed four additional carbon resonances: two methylenes ($\delta_C$ 29.8, 29.9) and two carbonyl carbons ($\delta_C$ 173.7, 176.1). Both methylenes showed HMBC correlations to the two carbonyl carbons, typical of a succinic acid moiety. These data indicated that BPL 88 was a succinic acid derivative of BPL 76. The position of the succinate was established at C-5 by the downfield shift of H-5, and by HMBC correlations of H-5 to both ketone C-4 and ester C-1" ($\delta_C$ 205.8 and 173.7, respectively), to give BPL 88 (FIG. 2A-2B). It was assumed that BPL 76 and BPL 88 had the same relative and absolute configurations based on similarities in chemical shifts and coupling constants.

BPL 88 characterization: colorless oil, [α]$^{25}_D$–1.5, (c 0.67, CHCl$_3$); IR (CHCl$_3$) $\nu_{max}$ 3436, 3028, 2933, 2860, 1726, 1459, 1375, 1268, 1167, 1091, 909 cm$^1$; $^1$H NMR see Table 2; $^{13}$C NMR see Table 3; HRESIMS m/z [M+H]$^+$ ion at 505.2078 (calcd for C$_{23}$H$_{37}$O$_{10}$S, 505.2107).

Structure Determination of BPL 81.

Figure 2C:
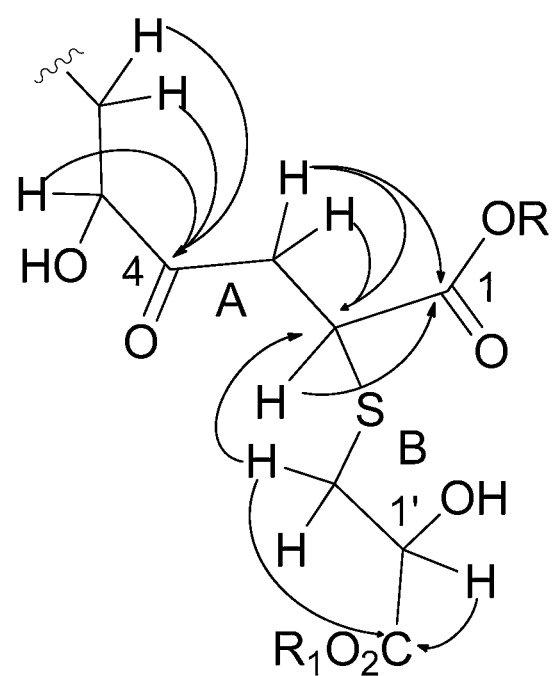
FIG. 2C shows selected long range correlations from the HMBC spectrum of BPL81.
Figure 2D:
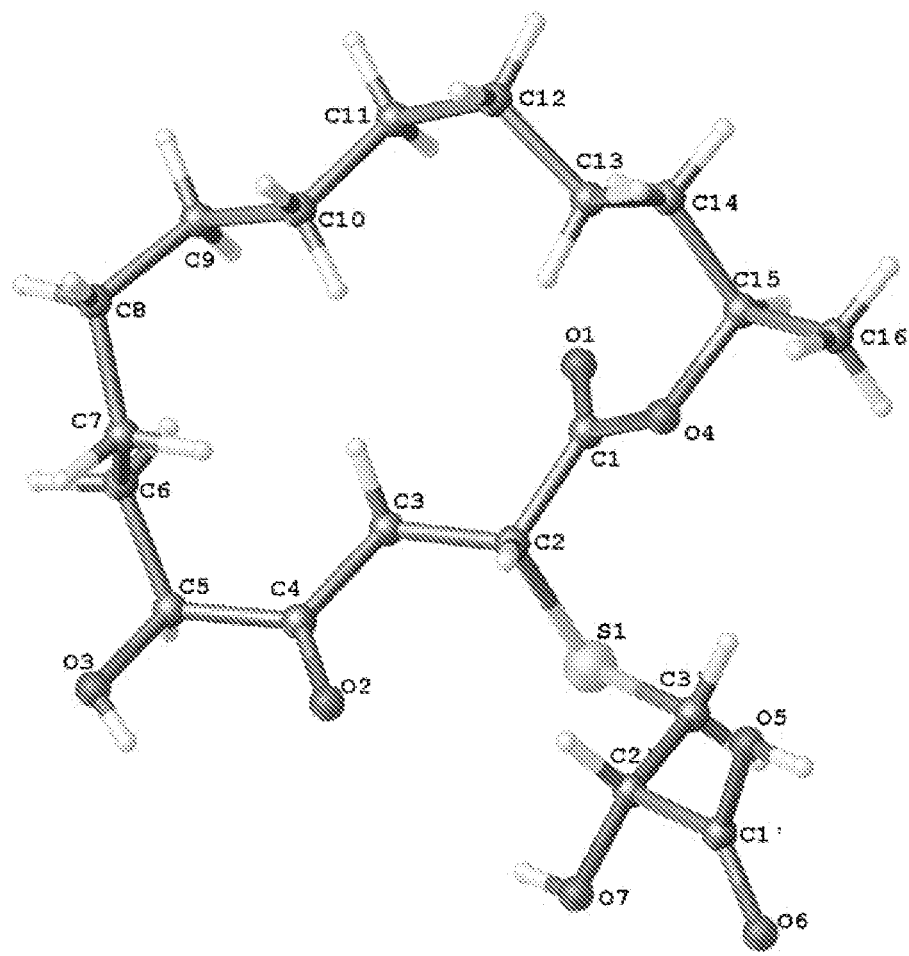
FIG. 2D shows the X-ray crystal structure of BPL76.

BPL 81 had a molecular formula of C$_{20}$H$_{30}$O$_7$ deduced from HRESIMS, with six sites of unsaturation. It was clear from the molecular formula that BPL 81 lacked the 3-mercaptolactate moiety found in BPL 76 and BPL 88. In the infrared spectrum, the carbonyl region of BPL 81 was more complex with overlapping carbonyl absorbances at 1745, 1734, 1716 and 1702 cm$^1$. Comparison of the $^1$H NMR and $^{13}$C NMR spectral data of compound BPL 88 with that of BPL 81 (Tables 2 and 3) showed the presence of the succinate moiety as well as an isolated, trans-disubstituted double bond C2-C3 [$\delta_C$ 133.3, $\delta_H$ 6.71, d (J=15.9 Hz); $\delta_C$ 137.3, $\delta_H$ 7.32, d (J=15.9 Hz)]. In the HMBC data, both olefinic H-2 and H-3 showed correlations to ketone C-4 ($\delta_C$ 197.7) and ester C-1 ($\delta_C$ 166.5). The upfield shift of these carbonyl carbons compared to those of BPL 76 and BPL 88 was consistent with α,β-unsaturation. These data suggested the structure of BPL 81 as shown in FIGS. 2B-2C. BPL 81 was previously reported in 1977 as the antibiotic A26771B, a metabolite of *Penicillium turbatum*. The NMR data of BPL 81 and A26771B in deuterated chloroform were virtually identical. There have been several total syntheses published for A26771B which have shown that the configurations at C-5 and C-15 are consistent with BPL 76 and BPL 88.

BPL 81 characterization: colorless oil, [α]$^{25}_D$–13° (c 0.055, CHCl$_3$); IR (CHCl$_3$) $\nu_{max}$ 3440, 3020, 2835, 1745, 1715, 1287, 1048 cm$^1$; $^1$H NMR see Table 2; $^{13}$C NMR see Table 3; HRESIMS m/z [M–H]$^-$ 381.1912 (calcd for C$_{20}$H$_{29}$O$_7$, 381.1913).

Structure Determination of BPL 77.

BPL 77 had a molecular formula of C$_{20}$H$_{30}$O$_8$ deduced from HRESIMS, with six sites of unsaturation. Even though BPL 77 has one more oxygen than BPL 81, the NMR spectral data were very similar. The main difference was the replacement of methylene C-14 in BPL 81 with an oxygen-bearing methine ($\delta_C$ 74.8, $\delta_H$ 3.50, m) in BPL 77. Methine H-14 was spin-coupled to both ester methine H-15 ($\delta_H$ 4.87, m) and to methylene H$_2$-13 ($\delta_H$ 1.56, m, 1.44, m), which supported positioning of the hydroxy group at C-14. Since the absolute configuration was assumed to be the same as that of the other macrolides, extensive molecular modeling studies were performed in Spartan'06ES to confirm the configuration at C-14 from coupling constant data. Both the C-14R and the C-14S epimers were subjected to Merck Molecular Force Field (MMFF) equilibrium conformation analysis to model the most stable conformer of each. The molecular modeling studies were inconclusive, probably due to the inherent flexibility of the lactone system. However, single crystal X-ray data on the related compound BPL 79 allowed us to ultimately assign the stereochemistry at C-14 as R.

BPL 77 characterization: colorless oil, $[\alpha]^{25}_D$ –0.9° (c 0.0300, CHCl$_3$); UV (MeOH) $\lambda_{max}$ (log ε) 224 (3.5) nm; IR (CHCl$_3$) $\nu_{max}$ 3416, 2928, 1744, 1702, 1288, 1163, 1043 cm$^{-1}$; $^1$H NMR see Table 2; $^{13}$C NMR see Table 3; HRESIMS m/z [M–H]$^-$ 397.1846 (calcd for C$_{20}$H$_{29}$O$_8$, 397.1862).

Structure Determination of BPL 78.

BPL 78 had a molecular formula of C$_{20}$H$_{30}$O$_8$ deduced by HRESIMS. BPL 77 and BPL 78 are isomers and their NMR spectral data is very similar (Tables 2 and 3). The main difference is a shift in the position of the hydroxy group from C-14 to C-13, which was supported by $^1$H-$^1$H COSY correlations. Oxygen-bearing methine H-15 ($\delta_H$ 5.23, m) was readily identified by its chemical shift and by its $^1$H-$^1$H-COSY correlation to methyl doublet H$_3$-16 ($\delta_H$ 1.35). H-15 was also spin-coupled to methylene H$_2$-14 ($\delta_H$ 1.89, m, 1.83, m) which were further coupled to hydroxy-bearing methine H-13 ($\delta_H$ 3.81, m). Molecular modeling studies were run to try to assign the absolute configuration of C-13 but were inconclusive.

BPL 78 characterization: colorless oil, $[\alpha]^{25}_D$ –18.0° (c 0.0051, CHCl$_3$); IR (CHCl$_3$) $\nu_{max}$ 3274, 2914, 1739, 1739, 1366, 1217 cm$^{-1}$; $^1$H NMR see Table 2; $^{13}$C NMR see Table 3; HRESIMS m/z [M–H]$^-$ 397.1862 (calcd for C$_{20}$H$_{29}$O$_8$, 397.1862).

TABLE 3

$^{13}$C NMR data for BPL 76, BPL 88, BPL 81, BPL 77, BPL 78 (100 MHz, MeOH-d$_4$).

| No | $\delta_C$, type BPL 76 | $\delta_C$, type BPL 88 | $\delta_C$, type BPL 81 | $\delta_C$, type BPL 77 | $\delta_C$, type BPL 78 |
|---|---|---|---|---|---|
| 1 | 174.2, C | 174.2, C | 166.5, C | 166.2, C | 166.2, C |
| 2 | 42.4, CH | 41.8, CH | 133.3, CH | 133.0, CH | 133.2, CH |
| 3 | 43.1, CH$_2$ | 43.6, CH$_2$ | 137.3, CH | 137.3, CH | 137.9, CH |
| 4 | 210.2, C | 205.8, C | 197.7, C | 197.5, C | 197.9, C |
| 5 | 76.8, CH | 78.7, CH | 79.5, CH | 79.3, CH | 79.3, CH |
| 6 | 33.6, CH$_2$ | 30.6, CH$_2$ | 30.1, CH$_2$ | 30.0, CH$_2$ | 30.0, CH$_2$ |
| 7 | 22.9, CH$_2$ | 23.4, CH$_2$ | 23.5, CH$_2$ | 24.9, CH$_2$ | 23.4, CH$_2$ |
| 8 | 27.9, CH$_2$ | 27.9, CH$_2$ | 28.3, CH$_2$ | 28.1, CH$_2$ | 28.5, CH$_2$ |
| 9 | 27.2, CH$_2$ | 27.2, CH$_2$ | 28.4, CH$_2$ | 28.1, CH$_2$ | 28.5, CH$_2$ |
| 10 | 28.1, CH$_2$ | 27.8, CH$_2$ | 29.3, CH$_2$ | 28.5, CH$_2$ | 29.2, CH$_2$ |
| 11 | 28.1, CH$_2$ | 28.3, CH$_2$ | 29.0, CH$_2$ | 29.3, CH$_2$ | 26.2, CH$_2$ |
| 12 | 26.4, CH$_2$ | 26.6, CH$_2$ | 28.7, CH$_2$ | 23.7, CH$_2$ | 36.8, CH$_2$ |
| 13 | 24.5, CH$_2$ | 24.4, CH$_2$ | 24.8, CH$_2$ | 33.4, CH$_2$ | 68.1, CH |
| 14 | 36.1, CH$_2$ | 36.0, CH$_2$ | 35.6, CH$_2$ | 74.8, CH | 42.6, CH$_2$ |
| 15 | 73.4, CH | 73.1, CH | 74.0, CH | 76.0, CH | 71.0, CH |
| 16 | 20.4, CH$_3$ | 20.3, CH$_3$ | 20.2, CH$_3$ | 17.9, CH$_3$ | 20.6, CH$_3$ |
| 1' | 175.9, C | 176.0, C | | | |
| 2' | 71.5, CH | 71.5, CH | | | |
| 3' | 36.7, CH$_2$ | 36.7, CH$_2$ | | | |
| 1" | | 173.7, C | 173.6, C | 173.6, C | 173.6, C |
| 2" | | 29.8, CH$_2$ | 29.8, CH$_2$ | 29.8, CH$_2$ | 29.8, CH$_2$ |
| 3" | | 29.9, CH$_2$ | 29.9, CH$_2$ | 29.9, CH$_2$ | 29.9, CH$_2$ |
| 4" | | 176.1, C | 175.9, C | 175.8, C | 175.9, C |

Structure Determination of BPL 84.

BPL 84 had a molecular formula of C$_{20}$H$_{32}$O$_7$ deduced from HRESIMS, with five sites of unsaturation. The NMR spectral data of BPL 84 indicated the presence of the succinate moiety as well as a conjugated double bond C2-C3 [$\delta_C$ 123.3, $\delta_H$ 6.10 dd (J=15.7, 1.8 Hz); $\delta_C$ 148.3, $\delta_H$ 6.93 dd (J=15.7, 4.9 Hz)] as in BPL 81, BPL 77, and BPL 78 (Tables 4 and 5). However, there was no evidence of a ketone carbon in the $^{13}$C NMR spectrum of BPL 84. Both olefinic protons H-2 and H-3 showed HMBC correlations to ester carbonyl

TABLE 2

$^1$H NMR data for BPL 76, BPL 88, BPL 81, BPL 77, BPL 78 (400 MHz, MeOH-d$_4$).$^a$

| No. | $\delta_H$, mult (J in Hz) BPL 76 | $\delta_H$, mult (J in Hz) BPL 88 | $\delta_H$, mult (J in Hz) BPL 81 | $\delta_H$, mult (J in Hz) BPL 77 | $\delta_H$, mult (J in Hz) BPL 78 |
|---|---|---|---|---|---|
| 2 | 3.90, dd (10.8, 4.0) | .86, dd (11.5, 3.4) | 6.71, d (15.9) | 6.72, d (15.9) | 6.71, d (15.9) |
| 3 | 3.21, dd (18.2, 10.8) | .24, dd (18.1, 1.5) | 7.32, d (15.9) | 7.33, d (15.9) | 7.34, d (15.9) |
|  | 2.88, dd (18.2, 4.0) | .89, dd (18.1, 3.4) | | | |
| 5 | 4.30, t (5.1) | .17, dd (6.0, 3.5) | 5.37, dd (5.9, 4.9) | 5.34, t (5.7) | 5.40, dd (6.1, 4.7) |
| 6 | 1.78, m | .86, m | 1.95, m | 1.89, m, 2H | 1.97, m |
|  | | | 1.87, m | | 1.84, m |
| 7 | 1.31, m | .30, m | 1.34, m | 1.47, m | 1.46, m |
|  | 1.13, m | | | | 1.20, m |
| 8 | 1.34, m | .34, m | 1.34, m | 1.34, m | 1.34, m |
| 9 | 1.34, m | .34, m | 1.34, m | 1.34, m | 1.34, m |
| 10 | 1.34, m | .34, m | 1.34, m | 1.34, m | 1.34, m |
| 11 | 1.34, m | .34, m | 1.34, m | 1.34, m | 1.34, m |
| 12 | 1.34, m | .34, m | 1.34, m | 1.34, m | 1.44, m |
| 13 | 1.34, m | .34, m | 1.34, m | 1.56, m | 3.81, m |
|  | | | | 1.44, m | |
| 14 | 1.64, m | .64, m | 1.72, m | 3.50, m | 1.89, m |
|  | 1.42, m | .42, m | 1.58, m | | 1.83, m |
| 15 | 4.95, m | .97, m | 5.13, m | 4.87, m | 5.23, m |
| 16 | 1.27, d (6.2) | .27, d (6.2) | 1.30, d (6.4) | 1.35, d (6.4) | 1.35, d (6.4) |
| 2' | 4.38, dd (6.7, 4.0) | .35, dd (6.6, 4.3) | | | |
| 3' | 3.21, dd (13.5, 4.0) | .21, dd (13.7, 4.3) | | | |
|  | 2.93, dd (13.5, 6.7) | .93, dd (13.7, 6.6) | | | |
| 2" | | .66, m | 2.70, m | 2.70, m | 2.70, m |
| 3" | | .60, m | 2.62 m | 2.62, m | 2.62, m |

$^a$All assignments are based on COSY, HSQC and HMBC experiments.

C-1 (δ$_C$ 167.8) and to an oxygen-bearing methine that resonated at δ$_C$ 73.0. The attached proton (δ$_H$ 4.55 m) showed HMBC correlations to C-2, C-3 and C-5 (δ$_C$ 77.8) as well as COSY coupling to methine H-5 (δ$_H$ 4.83 m). These data suggested that C-4 was reduced to an alcohol in macrolide BPL 84. The succinate moiety was again assigned to the C-5 position due to the chemical shift of H-5 and to a HMBC correlation between H-5 and succinate ester C-1".

BPL 84 characterization: colorless oil, [α]$^{25}_D$+9.0° (c 0.031, CHCl$_3$); IR (CHCl$_3$) ν$_{max}$ 3444, 3020, 1737, 1727, 1366, 1047 cm$^{-1}$; $^1$H NMR see Table 4; $^{13}$C NMR see Table 5; HRESIMS m/z [M−H]$^−$ 383.2069 (calcd for C$_{20}$H$_{31}$O$_7$, 383.2070).

Structure Determination of BPL 79.

Figure 2E:
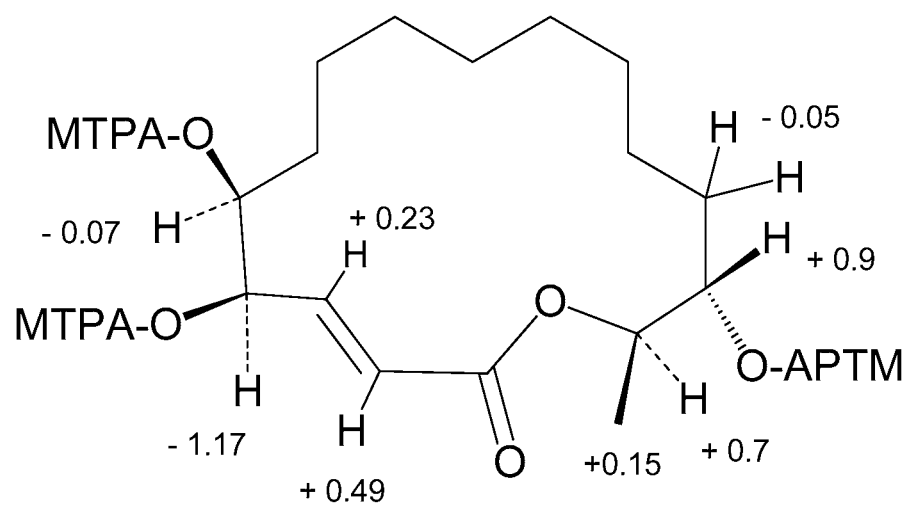
FIG. 2E shows selected δΔ values (chemical shift of the (S)-MTPA ester minus the chemical shift of the (R)-MTPA ester in ppm) of the (S) and (R)-MTPA esters of BPL79.

A molecular formula of C$_{16}$H$_{28}$O$_5$ was assigned to BPL 79 by HRESIMS. The NMR spectral data of BPL 79 were similar to that of BPL 84 (Tables 4 and 5). These data showed the typical resonances associated with the unsaturated cyclic macrolide structure, with a C-4 alcohol instead of a ketone, but lacked evidence of the succinate moiety. The $^1$H NMR data of BPL 79 showed an upfield shift of H-5 to δ$_H$ 3.61, which suggested a C-5 alcohol rather than a succinate ester. BPL 79 readily formed BPL 79 triacetate when treated with acetic anhydride-pyridine, indicating that BPL 79 is a triol. The third hydroxy group could be assigned to methine C-14 [δ$_C$ 75.0, δ$_H$ 3.42 td (J=8.5, 2.7 Hz)]. The COSY spectrum showed $^3$J-coupling of H-14 to ester methine H-15 [δ$_H$4.75 dq (J=8.5, 6.6)] which in turn was coupled to methyl H$_3$-16 [(δ$_H$ 1.33 d (6.6)]. Molecular modeling studies of BPL 79 indicated the same relative configuration at C-14 as found in BPL 77. The absolute configuration of BPL 79 was determined using a modified Mosher's method. In order to determine the configurations at C-4 and C-14, and to confirm that the configurations of C-5 and C-15 are consistent with BPL 76, compound BPL 79 was treated with R- or S-methoxy-(trifluoromethyl) phenylacetyl (MTPA) chloride in pyridine to give the corresponding S- or R-esters (S- and R-BPL79 MTPA ester) respectively. The results of this study are shown in FIG. 2E and established the absolute configuration of BPL 79 as 4R, 5S,14S,15R.

BPL 79 characterization: colorless solid, [α]$^{25}_D$+1.3° (c 0.101, CHCl$_3$); IR (solid) ν$_{max}$ 3200, 2916, 2850, 1706, 1275, 1043, 732 cm$^1$; $^1$H NMR see Table 4; $^{13}$C NMR see Table 5; HRESIMS m/z [M+H]$^+$ 301.2025 (calcd for C$_{16}$H$_{29}$O$_5$, 301.2015).

Figure 2F:
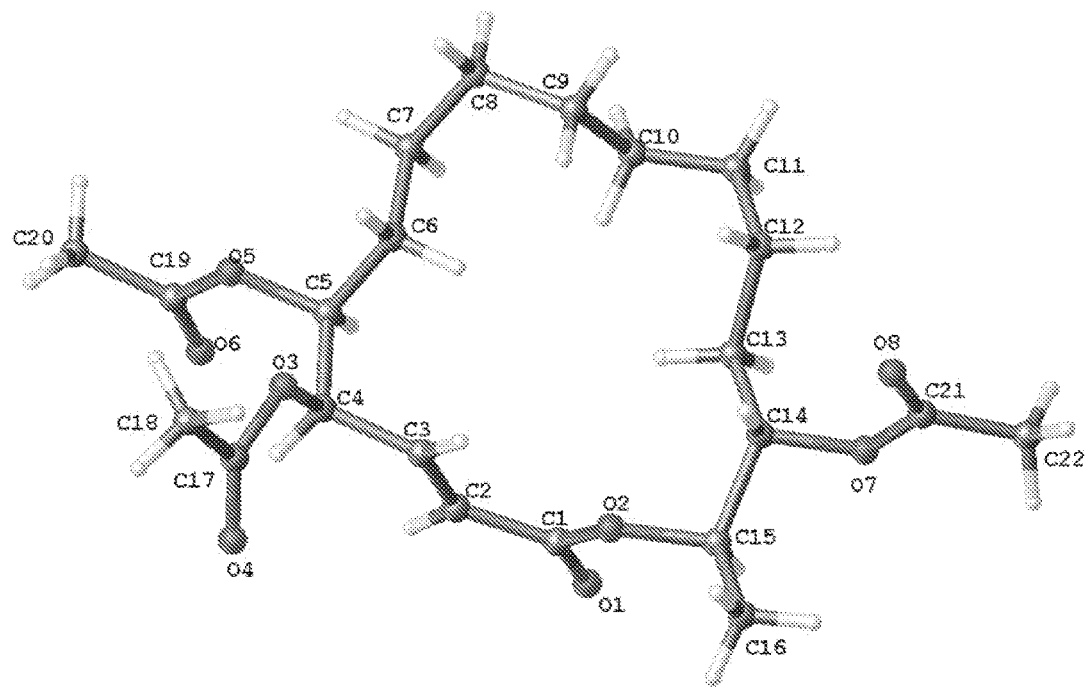
FIG. 2F shows the X-ray crystal structure of BPL79 triacetate.

A single crystal X-ray diffraction study of BPL 79 triacetate provided further confirmation of the structure and the relative and absolute configurations of BPL 79 (FIG. 2F). X-ray diffraction data for BPL 79 triacetate were collected at 100 K using CuKα (λ=1.54178) radiation. Data have been corrected for absorption using SADABS area detector absorption correction program. Using Olex2, the structure was solved with the ShelXT structure solution program using Direct Methods and refined with the ShelXL refinement package using least squares minimization. All non-hydrogen atoms were refined with anisotropic thermal parameters. All hydrogens were placed in calculated positions using a ridged group model with isotropic thermal parameters U(H)=1.2Ueq (C) for C(H) groups and U(H) =1.5Ueq (C) for all C(H,H,H) groups. The absolute structure was determined by refinement of the Flack Parameter, based on anomalous scattering, with a final Flack parameter of 0.05(8). Further analysis of the absolute structure performed using likelihood methods carried out with PLATON. The results were a final Hooft parameter of 0.04(6). All calculations and refinements were carried out using APEX2, SHELXTL, Olex2, and PLATON.

Crystallographic Data for BPL79 triacetate.

C$_{22}$H$_{34}$O$_8$, M=426.49, orthorhombic, space group P2$_1$2$_1$2$_1$, a=7.4360(3), b=9.5511(3), c=32.8373(11), V=2332.17, Z=4, T=100 K, μ(CuKα)=0.760 mm$^{-1}$, ρ$_{calcd}$=1.215 g ml$^{-1}$, 2θ$_{max}$=133.306, 18279 reflections measured, 4118 unique (R$_{int}$=0.0345, R$_{sigma}$=0.0279) R1=0.0535 (I>2σ(I)), wR2=0.1368 (all data), Flack Parameter=0.05(8), Hooft Parameter=0.04(6).

Structure Determination of BPL 86.

BPL 86 had a molecular formula of C$_{20}$H$_{32}$O$_8$ which was established by HRESIMS. The molecular formula of BPL 86 had four more carbons and hydrogens, and three more oxygens than BPL 79, suggesting the presence of a succinate moiety. The NMR spectral data was very similar to that of BPL 79, with the addition of the $^1$H and $^{13}$C resonances associated with the succinate moiety as in BPL 88, BPL 81, BPL 77, BPL 78, and BPL 84, and the downfield shift of H-5 (δ$_H$ 4.83), indicating the point of attachment (Tables 4 and 5). The COSY data showed that H-5 was coupled to H-4 (δ$_H$ 4.55), which was also coupled to olefin H-3 (δ$_H$ 6.95). Further confirmation was provided by an HMBC correlation between H-5 and succinate C-1" (δ$_C$ 174.2).

BPL 86 characterization: colorless oil, [α]$^{25}_D$−3.5° (c 0.051, CHCl$_3$); IR (CHCl$_3$) ν$_{max}$ 3421, 3020, 1732w, 1721, 1717, 1423, 1170, 1044, 929 cm$^1$; $^1$H NMR see Table 4; $^{13}$C NMR see Table 5; HRESIMS m/z [M−H]$^−$ 399.2006 (calcd for C$_{20}$H$_{31}$O$_8$, 399.2019).

Structure Determination of BPL 98.

The molecular formula of BPL 98 was established as C$_{20}$H$_{32}$O$_8$, by HRESIMS. BPL 98 and BPL 86 are isomers, and the NMR spectral data is very similar, with one major exception (Tables 3 and 5). There was no spectral evidence of the C-16 methyl group found in all of the other berkeleylactones. Instead, it was replaced by hydroxy-methylene C-16 (δ$_H$ 3.61, δ$_C$ 65.1). There is a strong COSY correlation between H$_2$-16 and ester methine H-15 (δ$_H$ 5.05) that supports this assignment. The absolute configurations at C-4, C-5 and C-15 again were assumed to be consistent with BPL 79.

BPL 98 characterization: colorless oil, [α]$^{25}_D$−23.5° (c 0.017, CHCl$_3$); IR (CHCl$_3$) ν$_{max}$ 3403, 3020, 1732, 1719, 1716, 1508, 1423, 1047, 929 cm$^{-1}$; $^1$H NMR see Table 4; $^{13}$C NMR see Table 5; HRESIMS m/z [M−H]$^−$ 399.2024 (calcd for C$_{20}$H$_{31}$O$_8$, 399.2019).

TABLE 4

$^1$H NMR data for BPL 84, BPL 79, BPL 86, BPL 98 (400 MHz, MeOH-d$_4$).$^a$

| No. | δ$_H$, mult (J in Hz) BPL 84 | δ$_H$, mult (J in Hz) BPL 79 | δ$_H$, mult (J in Hz) BPL 86 | δ$_H$, mult (J in Hz) BPL 98 |
|---|---|---|---|---|
| 2 | 6.10, dd (15.7, 1.8) | 6.05, dd (15.8, 1.7) | 6.09, dd (15.8, 1.6) | 6.17, dd (15.7, 1.8) |
| 3 | 6.93, dd (15.7, 4.9) | 6.95, dd (15.8, 5.0) | 6.95, dd (15.8, 4.9) | 6.97, dd (15.7, 4.5) |
| 4 | 4.55, m | 4.43, m | 4.55, m | 4.58, m |

TABLE 4-continued

¹H NMR data for BPL 84, BPL 79, BPL 86, BPL 98 (400 MHz, MeOH-d₄).[a]

| No. | $\delta_H$, mult (J in Hz) BPL 84 | $\delta_H$, mult (J in Hz) BPL 79 | $\delta_H$, mult (J in Hz) BPL 86 | $\delta_H$, mult (J in Hz) BPL 98 |
|---|---|---|---|---|
| 5 | 4.83, m | 3.61, m | 4.83, m | 4.84, m |
| 6 | 1.64, m | 1.59, m | 1.70, m | 1.71, m |
|   | 1.55, m | 1.26, m | 1.52, m | 1.50, m |
| 7 | 1.33, m | 1.34, m | 1.34, m | 1.33, m |
| 8 | 1.69, m | 1.34, m | 1.34, m | 1.33, m |
|   | 1.51, m |   |   |   |
| 9 | 1.33, m | 1.34, m | 1.34, m | 1.33, m |
| 10 | 1.33, m | 1.34, m | 1.34, m | 1.33, m |
| 11 | 1.33, m | 1.34, m | 1.34, m | 1.33, m |
| 12 | 1.33, m | 1.34, m | 1.34, m | 1.33, m |
| 13 | 1.33, m | 1.60, m | 1.37, m | 1.33, m |
|   |   | 1.37, m | 1.28, m |   |
| 14 | 1.33, m | 3.42, td (8.5, 2.7) | 3.41, td (7.9, 2.7) | 1.58, m |
|   |   |   |   | 1.52, m |
| 15 | 5.05, m | 4.75, dq (8.5, 6.6) | 4.77, m | 5.05, ddt (9.9, 5.5, 2.6) |
| 16 | 1.26, d (6.3) | 1.33, d (6.6) | 1.33, d (6.2) | 3.61, d (5.5) |
| 2" | 2.72, m |   | 2.63, bs | 2.63, bs |
| 3" | 2.65, m |   | 2.63, bs | 2.63, bs |

[a]All assignments are based on COSY, HSQC and HMBC experiments.

TABLE 5

¹³C NMR data for BPL 84, BPL 79, BPL 86, BPL 98 (100 MHz, MeOH-d₄).

| No | $\delta_C$, type BPL 84 | $\delta_C$, type BPL 79 | $\delta_C$, type BPL 86 | $\delta_C$, type BPL 98 |
|---|---|---|---|---|
| 1 | 167.8, C | 167.5, C | 167.3, C | 168.1, C |
| 2 | 123.3, CH | 122.5, CH | 123.1, CH | 123.1, CH |
| 3 | 148.3, CH | 149.9, CH | 148.7, CH | 148.7, CH |
| 4 | 73.0, CH | 75.7, CH | 74.6, CH | 73.0, CH |
| 5 | 77.8, CH | 75.2, CH | 77.9, CH | 77.8, CH |
| 6 | 30.4, $CH_2$ | 30.3, $CH_2$ | 30.4, $CH_2$ | 29.3, $CH_2$ |
| 7 | 24.8, $CH_2$ | 25.0, $CH_2$ | 24.1, $CH_2$ | 25.2, $CH_2$ |
| 8 | 27.3, $CH_2$ | 28.9, $CH_2$ | 27.4, $CH_2$ | 27.3, $CH_2$ |
| 9 | 28.6, $CH_2$ | 27.5, $CH_2$ | 29.1, $CH_2$ | 27.6, $CH_2$ |
| 10 | 27.5, $CH_2$ | 29.1, $CH_2$ | 27.6, $CH_2$ | 27.6, $CH_2$ |
| 11 | 28.4, $CH_2$ | 27.3, $CH_2$ | 27.5, $CH_2$ | 28.6, $CH_2$ |
| 12 | 27.6, $CH_2$ | 24.1, $CH_2$ | 24.9, $CH_2$ | 28.6, $CH_2$ |
| 13 | 25.3, $CH_2$ | 33.3, $CH_2$ | 33.4, $CH_2$ | 25.0, $CH_2$ |
| 14 | 36.8, $CH_2$ | 75.0, CH | 72.9, CH | 31.5, $CH_2$ |
| 15 | 72.5, CH | 74.6, CH | 75.1, CH | 76.5, CH |
| 16 | 20.9, $CH_3$ | 18.2, $CH_3$ | 18.2, $CH_3$ | 65.1, $CH_2$ |
| 1" | 174.2, C |   | 174.2, C | 174.2, C |
| 2" | 29.3, $CH_2$ |   | 28.7, $CH_2$ | 30.0, $CH_2$ |
| 3" | 29.9, $CH_2$ |   | 29.9, $CH_2$ | 30.5, $CH_2$ |
| 4" | 176.2, C |   | 176.2, C | 176.3, C |

Structure Determination of BPL 94.

BPL 94 had a molecular formula of $C_{16}H_{28}O_3$ deduced from HRESIMS, with three sites of unsaturation. The NMR spectral data of BPL 94 indicated the presence of the conjugated double bond C2-C3 as in BPL 81, BPL 77, and BPL 78 (Tables 6 and 7). However, there was no evidence of a ketone carbon in the ¹³C NMR spectrum of BPL 94. Both olefinic protons H-2 and H-3 showed HMBC correlations to ester carbonyl C-1 and to an oxygen-bearing methine that resonated at $\delta_C$ 71.1. The attached proton ($\delta_H$ 4.38 m) showed HMBC correlations to C-2, C-3 and C-5 as well as COSY coupling to methylene H-5 ($\delta_H$ 1.63 m). These data suggested that C-4 was reduced to an alcohol in macrolide BPL 94.

BPL 94 characterization: colorless oil; IR (CHCl₃) $\nu_{max}$ 3200, 2920, 2850, 1706, 1275, cm⁻¹; ¹H NMR see Table 6; ¹³C NMR see Table 7; HRESIMS m/z [M+23]⁺291.1858 (calcd for $C_{16}H_{28}O_3Na$, 291.1858).

Structure Determination of BPL 95. BPL 95 had a molecular formula of $C_{16}H_{28}O_4$ deduced from HRESIMS, with three sites of unsaturation. The NMR spectral data of BPL 95 indicated the presence of the conjugated double bond C2-C3 as in BPL 81, BPL 77, and BPL 78 (Tables 6 and 7). However, there was no evidence of a ketone carbon in the ¹³C NMR spectrum of BPL 95. Both olefinic protons H-2 and H-3 showed HMBC correlations to ester carbonyl C-1 and to an oxygen-bearing methine C-4 that resonated at $\delta_C$ 74.0. The attached proton H-4 ($\delta_H$ 4.46 m) showed HMBC correlations to C-2, C-3 and C-5 as well as COSY coupling to methine H-5 ($\delta_H$ 3.69 m). These data suggested that C-4 was reduced to an alcohol in macrolide BPL 95.

BPL 95 characterization: colorless oil; IR (CHCl₃) $\nu_{max}$ 3220, 2915, 1709, 1275 cm⁻¹; ¹H NMR see Table 6; ¹³C NMR see Table 7; HRESIMS m/z [M+23]⁺ 307.1831 (calcd for $C_{16}H_{28}O_4Na$, 307.1807).

Structure Determination of BPL 96.

BPL 96 had a molecular formula of $C_{20}H_{32}O_7$ deduced from HRESIMS, with five sites of unsaturation. The NMR spectral data of BPL 84 indicated the presence of the succinate moiety as well as a conjugated double bond C2-C3 as in BPL 81, BPL 77, and BPL 78 (Tables 6 and 7). There was no evidence of a ketone carbon in the ¹³C NMR spectrum of BPL 96. Both olefinic protons H-2 and H-3 showed HMBC correlations to ester carbonyl C-1 ($\delta_C$ 166.3) and to an oxygen-bearing methine C-4 that resonated at $\delta_C$ 76.5. The attached proton H-4 ($\delta_H$ 5.61 m) showed HMBC correlations to C-2, C-3 and C-5 ($\delta_C$ 72.9) as well as COSY coupling to methine H-5 ($\delta_H$ 3.78 m). These data suggested that C-4 was reduced to an alcohol in macrolide BPL 96. The succinate moiety was assigned to the C-4 position due to the chemical shift of H-4 and to a HMBC correlation between H-4 and succinate ester C-1".

BPL 96 characterization: colorless oil, $[\alpha]^{25}_D$ +9.0° (c 0.031, CHCl₃); IR (CHCl₃) $\nu_{max}$ 3440, 3022, 1733, 1725, 1715, 1360 cm⁻¹; ¹H NMR see Table 6; ¹³C NMR see Table 7; ESIMS m/z [M+23]⁺407, $C_{20}H_{32}O_7Na$.

TABLE 6

$^{13}$C NMR data for BPL 94, BPL 95, BPL 96 (400 MHz, CDCl$_3$).[a]

| No. | $\delta_H$, mult (J in Hz) BPL 94 | $\delta_H$, mult (J in Hz) BPL 95 | $\delta_H$, mult (J in Hz) BPL 96 |
|---|---|---|---|
| 2 | 5.96, dd (15.7, 1.2) | 6.05, d (15.8) | 5.98, d (15.8) |
| 3 | 6.87, dd (15.7, 6.4) | 6.88, dd (15.8, 5.3) | 6.82, dd (15.8, 5.6) |
| 4 | 4.38, m | 4.46, m | 5.61, m |
| 5 | 1.63, m | 3.69, m | 3.78, m |
| 6 | 1.55, m | 1.55, m | 1.65, m |
|   | 1.33, m | 1.33, m | 1.33, m |
| 7 | 1.33, m | 1.33, m | 1.33, m |
| 8 | 1.33, m | 1.33, m | 1.33, m |
|   | 1.33, m | 1.33, m | 1.33, m |
| 9 | 1.33, m | 1.33, m | 1.33, m |
| 10 | 1.33, m | 1.33, m | 1.33, m |
| 11 | 1.33, m | 1.33, m | 1.33, m |
| 12 | 1.33, m | 1.33, m | 1.33, m |
| 13 | 1.33, m | 1.33, m | 1.33, m |
|   | 1.33, m | 1.33, m | 1.33, m |
| 14 | 1.33, m | 1.33, m | 1.33, m |
|   | 1.33, m | 1.33, m | 1.33, m |
| 15 | 5.02, m | 5.00, m | 5.00, m |
| 16 | 1.25, d (6.3) | 1.24, d (6.3) | 1.24, d (6.3) |
| 2" |  |  | 2.70, m |
| 3" |  |  | 2.70, m |

[a]All assignments are based on COSY, HSQC and HMBC experiments.

TABLE 7

$^{13}$C NMR data for BPL 94, BPL 95, BPL 96 (100 MHz, CDCl3).[a]

| No | $\delta_C$, type BPL 94 | $\delta_C$, type BPL 95 | $\delta_C$, type BPL 96 |
|---|---|---|---|
| 1 | 166.0, C | 166.1, C | 166.3, C |
| 2 | 122.0, CH | 122.5, CH | 124.0, CH |
| 3 | 149.2, CH | 145.6, CH | 141.1, CH |
| 4 | 71.1, CH | 74.0, CH | 76.5, CH |
| 5 | 35.5, CH$_2$ | 73.9, CH | 72.9, CH |
| 6 | 30.4, CH$_2$ | 30.4, CH$_2$ | 30.4, CH$_2$ |
| 7 | 24.8, CH$_2$ | 24.8, CH$_2$ | 24.8, CH$_2$ |
| 8 | 27.3, CH$_2$ | 27.3, CH$_2$ | 27.3, CH$_2$ |
| 9 | 28.6, CH$_2$ | 28.6, CH$_2$ | 28.6, CH$_2$ |
| 10 | 27.5, CH$_2$ | 27.5, CH$_2$ | 27.5, CH$_2$ |
| 11 | 28.4, CH$_2$ | 28.4, CH$_2$ | 28.4, CH$_2$ |
| 12 | 27.6, CH$_2$ | 27.6, CH$_2$ | 27.6, CH$_2$ |
| 13 | 25.3, CH$_2$ | 25.3, CH$_2$ | 25.3, CH$_2$ |
| 14 | 35.2, CH$_2$ | 35.2, CH$_2$ | 35.2, CH$_2$ |
| 15 | 71.3, CH | 71.3, CH | 71.6, CH |
| 16 | 20.4, CH$_3$ | 20.4, CH$_3$ | 20.4, CH$_3$ |
| 1" |  |  | 171.6, C |
| 2" |  |  | 28.9, CH$_2$ |
| 3" |  |  | 29.2, CH$_2$ |
| 4" |  |  | 176.3, CH |

[a]All assignments are based on COSY, HSQC and HMBC experiments.

Compounds of the invention may be prepared as illustrated in the following schemes and examples.

Synthesis of BPL 76 Methyl Ester.

BPL 76 (0.5 g) was dissolved in diethylether (100 μL) and a solution of diazomethane in diethylether was added drop wise until the solution stayed yellow. After that time the solvent was removed to give methylated BPL 76 as an oil (0.5 g). $^1$H NMR (CDCl$_3$) $\delta_c$=4.95 (1H, m, H-15), 4.48 (1H, dd, J=5.6, 3.7 Hz, H-2'), 4.34 (1H, t, J=4.1 Hz, H-5), 4.01 (1H, dd, J=8.2, 6.1 Hz, H-2), 3.79 (3H, s, OMe), 3.25 (1H, m, H-3), 3.21 (1H, m, H-3'), 2.95 (1H, dd, J=14.3, 5.8 Hz, H-3'), 2.72 (1H, dd, J=18.5, 6.1 Hz, H-3), 1.84 (2H, m, H-6), 1.26 (3H, d, J=6.2 Hz, H-16); ESIMS 419 [M+1].

Synthesis of BPL 76 Diacetate.

Methylated BPL 76 (0.5 mg) was dissolved in pyridine (30 μL) and acetic anhydride (30 μL) and stirred for 24 h. The solvents were removed in vacuo to give acetylated BPL 76 as an oil (0.5 mg). $^1$H NMR (CDCl$_3$) $\delta_H$ 5.31 (1H, dd, J=7.3, 3.8 Hz, H-2'), 5.05 (1H, t, J=4.8 Hz, H-5), 4.99 (1H, p, J=6.2 Hz, H-15), 3.88 (1H, dd, J=11.3, 3.3 Hz, H-2), 3.75 (3H, s, OMe), 3.25 (1H, dd, J=7.6, 3.6 Hz, H-3), 3.20 (1H, m, H-3'), 3.02 (1H, dd, J=14.4, 7.5 Hz, H-3), 2.80 (1H, dd, J=18.1, 3.4 Hz, H-3'), 2.15 (3H, s, OAc), 2.08 (3H, s, OAc), 1.25 (3H, d, J=6.3 Hz, H-16); HRESIMS m/z [M+Na]$^+$ 525.2119 (calcd for C$_{24}$H$_{38}$O$_9$NaS, 525.2134).

Synthesis of BPL 79 Triacetate.

BPL 79 (0.5 mg) was dissolved in pyridine (30 μL) and acetic anhydride (30 μL) and stirred for 24 hours. After that time the solvents were removed to give BPL 79 triacetate as an oil (0.5 mg). $^1$H NMR (CDCl$_3$): δ 6.83 (1H, dd, J=15.9, 5.5 Hz, H-3), 6.02 (1H, dd, J=15.8, 1.7 Hz, H-2), 5.72 (1H, dt, J=5.4, 2.0 Hz, H-4), 4.98-5.06 (1H, m, H-15), 4.91 (1H, ddd, J=7.9, 5.1, 2.3 Hz, H-5), 4.86 (1H, td, J=7.6, 3.9 Hz, H-14), 2.12 (3H, s, Ac), 2.05 (3H, s, Ac), 2.04 (3H, s, Ac), 1.23 (3H, d, J=6.3 Hz, H-16); ESIMS m/z [M+1]$^+$427, m/z [M+Na]$^+$449.

Chiral Derivatization of BPL 79.

BPL 79 (1.0 mg) was dissolved in dry pyridine (40 μL) and either the R or S stereoisomer of α-methoxy-α-trifluoromethylphenylacetyl chloride (4 μL) added. The mixtures were stirred for 24 hours. After that time, methanol (400 μL), was added and the solvents removed. The reaction mixtures were then each passed through a small silica gel column and eluted with hexane and increasing amounts of IPA to give the products. (S)-MTPA ester-$^1$H NMR (selected shifts) (CDCl$_3$): δ 7.32-7.41 (m, aromatics), 6.85 (1H, dd, J=15.9, 4.5 Hz, H-3), 6.10 (1H, dd, J=15.9, 1.8 Hz, H-2), 5.09 (1H, m, H-5), 5.05 (1H, m, H-14), 5.02 (1H, m, H-15), 4.65 (1H, m, H-4), 1.23 (3H, d, J=6.2, H-16); ESIMS 949 [M+1]. (R)-MTPA ester-$^1$H NMR (selected shifts) (CDCl$_3$) δ 7.32-7.41 (m, aromatics), 6.62 (1H, dd, J=15.9, 5.0 Hz, H-3), 5.82 (1H, m, H-4), 5.61 (1H, dd, J=15.9, 1.6 Hz, H-2), 5.16 (1H, m, H-5), 4.98 (1H, m, H-14), 4.93 (1H, m, H-15), 1.08 (3H, d, J=6.0, H-16); ESIMS 949 [M+1].

Synthesis of BPL 81 macrolactams.

Synthesis of the BPL81 macrolactam can be accomplished using Grubbs I catalyzed metathesis to generate the scaffold from precursors assembled using Grignard reactions. This methodology facilitates replacement of the lactone moiety with the lactam and can also facilitate changes in ring size, as varying Grignard reagents can be used to introduce variations in ring size.

Scheme I

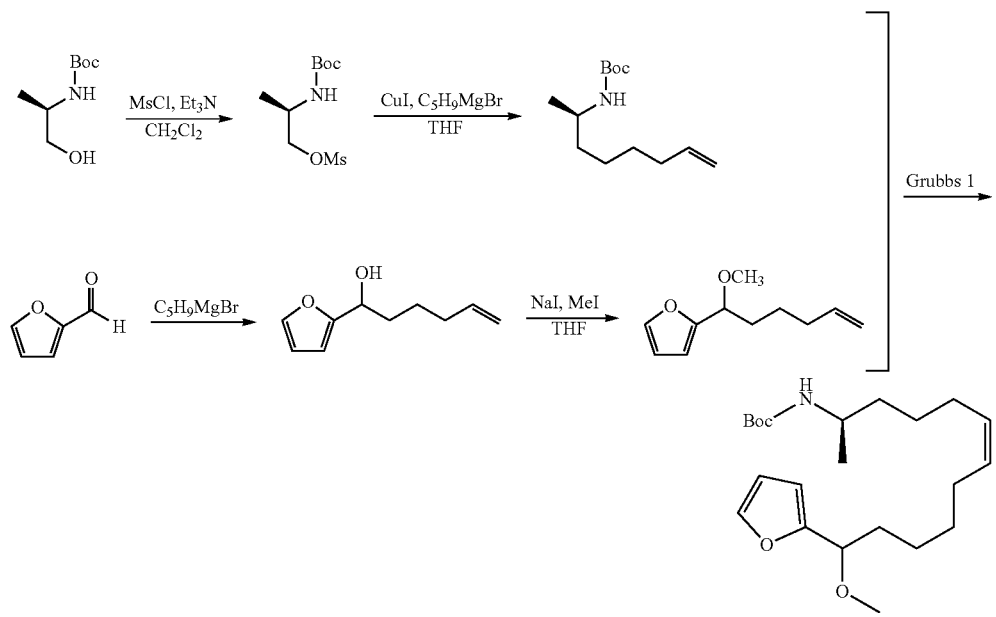

In Scheme I of the lactam synthesis, Grignard reactions and Grubbs 1-catalyzed metathesis will be used to synthesize the BOC-protected intermediate as described in Canova, S.; Lepine, R.; Thys, A.; Baron, A.; Roche, D. 2011 *Synthesis and biological properties of macrolactam analogs of the natural product macrolide (−)-A26771B*. Bioorg. Med. Chem. Lett. 21:4768-4772. The Grignard reactions determine the size of the lactam ring which can be varied in future iterations of analog development.

a carboxylic acid. Boc-deprotection followed by lactamisation using HATU, a reagent used in peptide coupling chemistry, will yield the desired macrolactam.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups,

Scheme II

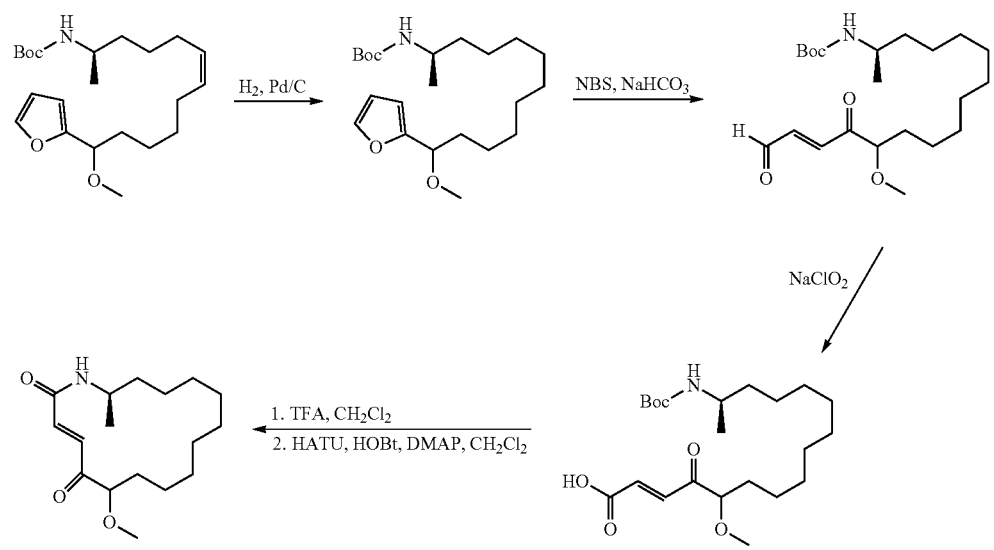

In Scheme II the intermediate obtained in Scheme I is cyclized through a series of steps that includes opening of the furan ring under Kobayashi conditions followed by sodium chlorite oxidation of the resulting aldehyde to form by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

Figure 2G:
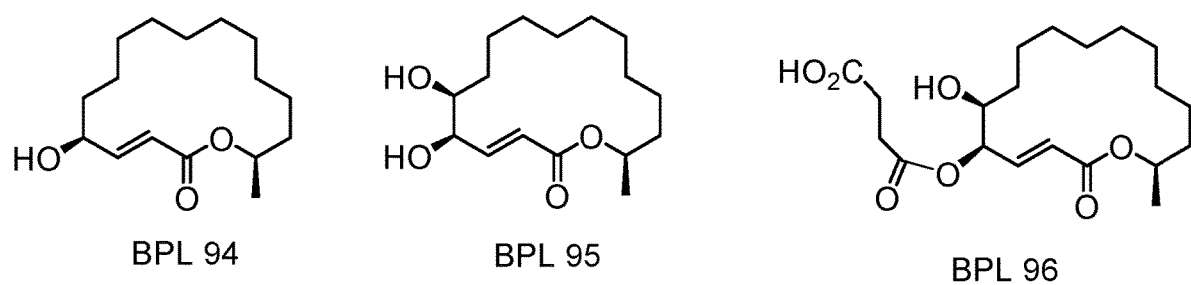
FIG. 2G shows the representative structures for derivatives of BPL76.
Figure 3:
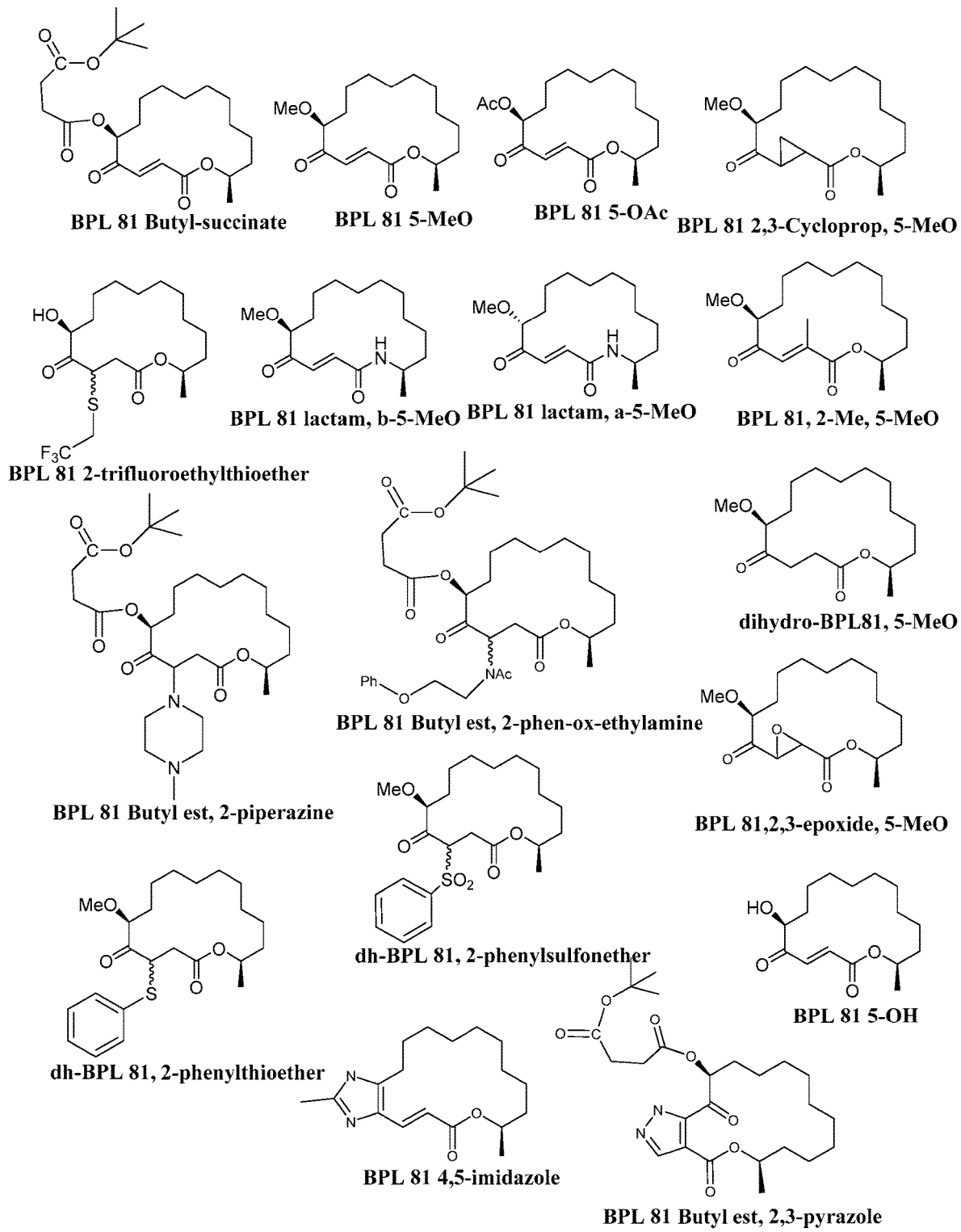
FIG. 3 shows derivatives of BPL 81 that have been used or are contemplated for use as an antibiotic.

Using procedures analogous to the foregoing schemes and examples, additional compounds of formula (I) may be prepared, including those in FIG. 2B and FIG. 2G. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

6. Biological Methods and Evaluation

Macrolide Inhibition of Protein Synthesis.

Conventional macrolide antibiotics block bacterial protein biosynthesis by binding to the 23S ribosomal RNA of the 50S subunit and interfering with the elongation of nascent peptide chains during translation. BPL 76, erythromycin, josamycin, and tylosin were evaluated in the extension inhibition assay (toeprinting) which identifies stalled ribosomes on mRNA. Under normal conditions, the reverse transcriptase creates a complete cDNA copy of the mRNA of interest. However, when the reverse transcriptase is blocked by bound ribosomes, shorter cDNA fragments, called toeprints, are created and able to be visualized as distinct fragments when compared to the full length cDNA copy on a standard sequencing gel.

Figure 4A:
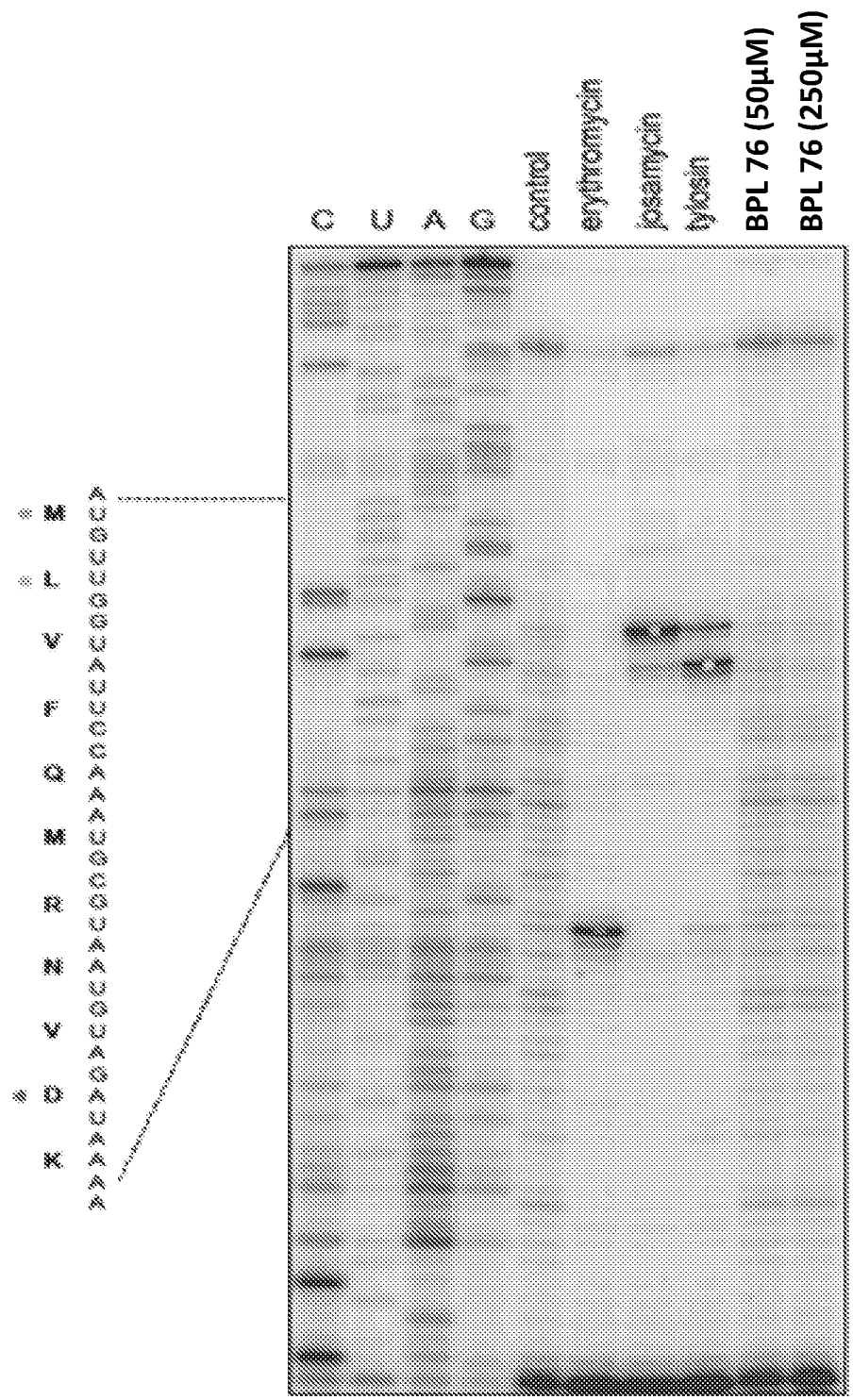
FIG. 4A shows the comparison of protein synthesis inhibition by known macrolide antibiotics and lack of inhibition by BPL 76 in an extension inhibition assay.

Toeprinting can assess the ability of a specific antibiotic to stall a ribosome at a specific mRNA codon. It can also give direct evidence of the mode of action of an antibiotic. The inducible genes of macrolide antibiotic resistance, including ermB (erythromycin ribosome methylase B), are regulated by cofactor-dependent programmed translation arrest. In the case of antibiotic resistance, ORF ermBL is constitutively translated and the macrolide resistance gene ermB is constitutively attenuated. Known macrolide antibiotics stall the ribosome during translation of ermBL which allows expression of ermB, and subsequent antibiotic resistance. BPL 76 did not induce stalling of the ribosome at the ermBL ORF unlike the comparative macrolide antibiotics (FIG. 4A).

Figure 4B:
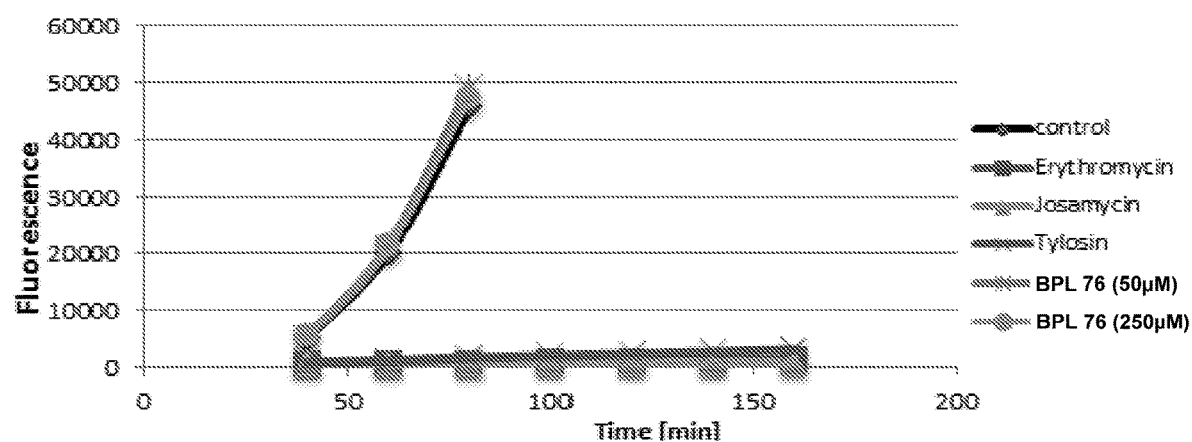
FIG. 4B shows the comparison of protein synthesis inhibition by known macrolide antibiotics and lack of inhibition by BPL 76 in a cell-free translation assay using a green fluorescent protein (GFP) reporter.

Further assessment of the effect of BPL76 on protein translation was done using a cell-free translation assay. The plasmid pY71-sfGFP[55] (5 ng) was translated in the PURE-express in vitro protein synthesis system (New England Biolabs). The final concentrations of erythromycin, josamycin and tylosin in the translation reactions were 50 µM. BPL 76 was tested at 50 µM and 250 µM, as indicated in FIG. 4B. The reactions were incubated at 37° C. and fluorescence readings (excitation: 488 nm, emission, 520 nm) were taken every 20 min for 2 hr. Known macrolide antibiotics erythromycin, josamycin and tylosin effectively inhibited the GFP synthesis and the corresponding fluorescence whereas BPL 76 had no effect at either concentration (FIG. 4B) and produced results comparable to that of the control lacking antibiotic. Taken together these results strongly suggest that BPL 76 does not inhibit bacterial protein synthesis.

Antibiotic Activity of Macrolides.

The isolated macrolide compounds were tested for activity against a panel of Gram-positive and Gram-negative bacteria and three *Candida* isolates at concentrations of 1 μM-1 mM/well (FIG. 5) to determine a minimum inhibitory concentration or the lowest drug concentration capable of causing growth inhibition of greater than or equal to 90% relative to the growth for the drug-free controls. BPL 76 exhibited the strongest activity against Gram-positive bacteria. None of this collection of compounds were active against Gram-negative bacteria The derivatives of BPL 76 were tested against a similar panel of microbial species as described above (Table 8). The methyl ester showed little change in the effectiveness against *Staphylococcus aureus, Streptococcus pyogenes* or *Candida glabrata* as compared to BPL76. However, increased effectiveness was shown for *Bacillus subtilis, C. albicans, B. anthracis* and EF. Conversely, the diacetate version of BPL 76 showed similar or decreased effectiveness against all microbial species tested except for *Bacillus subtilis* where the MIC was almost half that of BPL 76.

The derivatives of BPL 79 and BPL 84 were also tested against a similar panel as the isolated macrolide compounds (Table 9). BPL 95, the BPL 79 derivative lacking a hydroxyl at the C14 position (FIG. 2G), performed similarly against all microbes tested but, most notably, was not nearly as effective against *Staphylococcus aureus* as BPL79. BPL 94, the BPL 79 derivative lacking hydroxyl moieties at the C5 and C14 positions (FIG. 2G), was more effective against *Streptococcus pyogenes, Bacillus subtilis* and *B. anthracis* than BPL 79. However, similar to BPL 95, it was less effective again *Staphylococcus aureus*. The positional derivative of BPL 84, BPL 96 (FIG. 2G), was also tested as above (Table 9). BPL 96 showed similar effectiveness as BPL 84 across the entire panel of microbes tested but was most effective against *Bacillus subtilis* but not nearly as effective as some of the isolated macrolides in FIG. 5.

BPL 76 was even more active against four MRSA strains than it was against a methicillin-susceptible strain of *Staphylococcus aureus* (Table 10). Both the methyl ester and the diacetate derivatives of BPL 76 slightly less but still very strong activity against the same four MRSA strains (Table 11). The activities of compounds BPL 76 and BPL 81 were compared to several known antibiotics against three methicillin-resistant strains of *S. aureus* [FIG. 6, comparative data provided by Hartford Hospital, Center for Anti-Infective Research and Development (CAIRD)].

Additionally, BPL 76 and derivatives were tested against a panel of gram negative bacteria including *K. pneumonia, P. aeruginosa* and *E. coli* (Table 12). While most derivatives demonstrated no activity against these isolates, BPL 76 and BPL 77 were weakly active against *K. pneumonia* and *E. coli*. Interestingly, methylation of BPL 76 resulted in 4-5× fold increases in potency for antimicrobial activity against these pathogens, suggesting derivatization of this core compound is important for modulating its broad spectrum activity.

Additionally, BPL 81 and derivatives were tested against a panel of gram positive and gram negative bacteria (FIG. 7). While most derivatives demonstrated little to no activity against the gram negative bacteria some of the derivatives had very interesting results against some of the gram positive isolates tested.

TABLE 8

Antibiotic testing data of BPL76 derivatives.

| | *Staphylococcus aureus* (13709) μg/mL | *Streptococcus pyogenes* μg/mL | *Candida glabrata* μg/mL | *Bacillus subtilis* μg/mL | *C. albicans* μg/mL | *B. anthracis* μg/mL | *Enterococcus faecalis* μg/mL |
|---|---|---|---|---|---|---|---|
| BPL 76 | 1 | 3 | 6 | 13 | 26 | 3 | 13 |
| BPL 76-Me ester | 1 | 3 | 7 | 3 | 13 | 1 | 3 |
| BPL 76-diacetate | 2 | 15 | >125 | 7 | >125 | 4 | 15 |
| BPL 88 | 4 | 119 | 31 | 31 | >119 | 8 | 31 |

TABLE 9

Antibiotic testing data of BPL 84 and BPL 79 derivatives.

| | *Staphylococcus aureus* (13709) μg/mL | *Streptococcus pyogenes* μg/mL | *Candida glabrata* μg/mL | *Bacillus subtilis* μg/mL | *C. albicans* μg/mL | *B. anthracis* μg/mL |
|---|---|---|---|---|---|---|
| BPL 81 | 3 | 48 | 48 | 12 | 96 | 6 |
| BPL 84 | 45 | >90 | >90 | >90 | >90 | >90 |
| BPL 79 | 19 | 150 | >300 | >300 | >300 | 75 |
| BPL 86 | 24 | >50 | >50 | >50 | >50 | 24 |
| BPL 98 | >100 | >100 | >100 | >100 | >100 | >100 |
| BPL 94 | 34 | 67 | >67 | 34 | >67 | 34 |
| BPL 95 | 48 | >96 | >96 | 48 | >96 | >96 |
| BPL 96 | 48 | >96 | >96 | 48 | >96 | >96 |

TABLE 10

Antibiotic testing data of selected berkeleylactones against methicillin-resistant strains of S. aureus.

|  | S. aureus CAIRD116 | | S. aureus CAIRD142 | | S. aureus CAIRD148 | | S. aureus (NE277) | |
| --- | --- | --- | --- | --- | --- | --- | --- | --- |
|  | µM | µg/mL | µM | µg/mL | µM | µg/mL | µM | µg/mL |
| BPL 76 | 2 | 1 | 4 | 2 | 2 | 1 | 2 | 1 |
| BPL 88 | 32 | 15 | 32 | 15 | 16 | 8 | 16 | 8 |
| BPL 81 | 16 | 6 | 16 | 6 | 16 | 6 | 16 | 6 |
| BPL 84 | >250 | >90 | >250 | >90 | >250 | >90 | >250 | >90 |
| BPL 86 | 125 | 47 | 125 | 47 | 125 | 47 | 125 | 47 |
| BPL 98 | >250 | >100 | >250 | >100 | >250 | >100 | >250 | >100 |

TABLE 11

Antibiotic testing data of BPL 76 derivatives against methicillin-resistant strains of S. aureus.

|  | S. aureus CAIRD116 µg/mL | S. aureus CAIRD142 µg/mL | S. aureus CAIRD148 µg/mL | S. aureus (NE277) µg/mL |
| --- | --- | --- | --- | --- |
| BPL 76 | 1 | 2 | 1 | 1 |
| BPL 76-Me ester | 2 | 2 | 2 | 2 |
| BPL 76-diacetate | 4 | 7 | 4 | 4 |
| BPL 88 | 15 | 15 | 8 | 8 |

TABLE 12

Antibiotic testing data of BPL 76 derivatives against gram negative bacteria.

|  | K. pneumoniae (10031) | | P. aeruginosa MIC | | E. coli (25922) | |
| --- | --- | --- | --- | --- | --- | --- |
|  | µM | µg/mL | µM | µg/mL | µM | µg/mL |
| BPL 76 | 1000 | 404.518 | >1000 |  | 1000 | 404.518 |
| BPL 77 | 1000 | 398.447 | >1000 |  | 500 | 199.224 |
| BPL 78 | >1000 |  | >1000 |  | >1000 |  |
| BPL 79 | >1000 |  | >1000 |  | >1000 |  |
| BPL 81 | >250 |  | >250 |  | >250 |  |
| BPL 76 Me | 250 | 104.636 | >250 |  | 125 | 52.318 |
| BPL 76 Me Ac | >125 |  | >125 |  | >125 |  |
| BPL 86 Me Ac | >250 |  | >250 |  | >250 |  |
| BPL 84 Me Ac | >500 |  | >500 |  | >500 |  |
| BPL 79 Ac | >500 |  | >500 |  | >500 |  |
| BPL 88 | >250 |  | >250 |  | >250 |  |
| BPL 84 | >250 |  | >250 |  | >250 |  |
| BPL 86 | >125 |  | >125 |  | >125 |  |

Macrolide Antibiotic Activity Against Replication *Mycobacterium tuberculosis*.

A colorimetric, microplate-based Alamar Blue assay (MABA) method was used to determine the MICs of a selection of BPL compounds and known antibiotics for *Mycobacterium tuberculosis* (Mtb). In addition, the antimicrobial activity of the same compounds against Mtb grown under hypoxic conditions was assessed using a low oxygen recovery assay (LORA). LORA is a bioassay developed to screen antimicrobial agents against the physiological state of non-replicating persistence *Mycobacterium tuberculosis* (NRP-TB) responsible for antimicrobial tolerance in many bacterial infections whereas MABA measures the activity against a replicating form of *Mycobacterium tuberculosis*.

Alamar Blue is a redox indicator that yields a colorimetric change and a fluorescent signal in response to metabolic activity. It is a general indicator of cellular growth and/or viability; the blue, non-fluorescent, oxidized form becomes pink and fluorescent upon reduction. Growth can therefore be measured with a fluorometer or spectrophotometer or determined by a visual color change. Methods of using the MABA assay have been developed and successfully used for accurately measuring the minimum inhibitory concentration (MIC) of antimicrobial compounds on strains of *Mycobacterium* (see, for example, Collins and Franzblau (1997) "Microplate Alamar Blue assay versus Bactec 460 system for high-throughput screening of compounds against *Mycobacterium tuberculosis* and *Mycobacterium avium*" Antimicrobial Agents and Chemotherapy 41(5): 1004 or Cho S1, Lee H S, Franzblau S. Microplate Alamar Blue Assay (MABA) and Low Oxygen Recovery Assay (LORA) for *Mycobacterium tuberculosis*. Methods Mol Biol. 2015, 1285:281-92).

Briefly, bacterial cultures with an OD600 between 0.5-0.9 were diluted to OD600 of 0.015-0.02 into standard growth medium. In a 96-well microtiter plate, 200 µl of sterile Millipore water was added to all perimeter wells and 100 µl of standard liquid media was added to all inner wells. Diluted culture (100 µl) was added to each well, which were pre-aliquoted with various concentrations of the antibiotic or BPL compound. Initial dilutions were prepared in either dimethyl sulfoxide or distilled deionized water, and subsequent two-fold dilutions were performed in 0.1 ml of 7H9GC (no Tween 80) in the microplates. Wells containing antibiotic only were used to detect autofluorescence of compounds. Additional control wells consisted of bacteria only (B) and medium only (M).

Plates were incubated at 37° C. Starting at day 4 of incubation, 20 ml of 103 Alamar Blue solution (Alamar Biosciences/Accumed, Westlake, Ohio) and 12.5 ml of 20% Tween 80 were added to one B well and one M well, and plates were reincubated at 37° C. Wells were observed at 12 and 24 h for a color change from blue to pink and for a reading of ≥50,000 fluorescence units (FU). Fluorescence was measured in a Cytofluor II microplate fluorometer (PerSeptive Biosystems, Framingham, Mass.) in bottom-reading mode with excitation at 530 nm and emission at 590 nm. If the B wells became pink by 24 h, reagent was added to the entire plate. If the well remained blue or <50,000 FU was measured, additional M and B wells were tested daily until a color change occurred, at which time reagents were added to all remaining wells. Plates were then incubated at 37° C., and results were recorded at 24 h post-reagent addition. Visual MICs were defined as the lowest concentration of drug that prevented a color change. For fluorometric MICs, a background subtraction was performed on all wells with a mean of triplicate M wells. The lowest drug concentration effecting an inhibition of ≥90% was considered the MIC.

Low Oxygen Recovery Assay was completed as essentially described in Cho S1, Lee H S, Franzblau S. Microplate Alamar Blue Assay (MABA) and Low Oxygen Recovery Assay (LORA) for *Mycobacterium tuberculosis*. Methods Mol Biol. 2015, 1285:281-92.

The MABA and LORA assay results demonstrated that while one of the derivatives was not active against either replicating or non-replicating Mtb, such as BPL84, most derivatives demonstrated at least some activity against one or the other (Table 13). The most active compound was BPL 76 which demonstrated a MIC against both replicating and non-replicating Mtb of ~25-24 µg/ml. This was 25 fold less active than against MRSA and 100× time less potent than the currently used rifampicin.

TABLE 13

Minimum Inhibitory Concentrations (MICs) of BPL compounds and known antibiotics for *Mycobacterium tuberculosis* as determined under normal (MABA) and non-replicating persistence (LORA) conditions.

|  | MABA | LORA |
|---|---|---|
|  | MIC (µg/mL) | |
| BPL 76 | 25 | 24 |
| BPL 81 | 47 | >100 |
| BPL 84 | >100 | >100 |
| BPL 76 Methyl Ester | 32 | 19 |
| BPL 88 | >100 | 46 |
| BPL 94 | 39 | 20 |
| BPL 95 | >100 | 24 |
|  | MIC (µM) | |
| RMP - Rifampicin | >0.1 | 0.4 |
| INH - Isoniazid | 0.5 | >128 |
| LIZ - Linezolidum | 2 | 2 |
| MOX - Moxifloxicin | 0.2 | — |
| MET - Metronidazole | — | 449 |
| PA824 | 0.2 | 7 |
| TMC207 | >0.1 | 0.1 |

Cytotoxicity of Macrolide Antibiotics.

Cytotoxicity for Vero, HepG2 and J774 cells were determined following 72 hours exposure to BPL76 and analogs. Cell viability was assessed on the basis of cellular conversion of MTS dye into a soluble formazan product using the Promega CellTiter 96 Aqueous Non-Radioactive Cell Proliferation Assay. After incubation at 37° C. for 72 h, medium was removed and monolayers were washed twice with 100 µl of warm Hanks' balanced salt solution (HBSS). One hundred microliters of warm medium and 20 µl of freshly made MTS-PMS [3-(4,5-dimethylthiazol-2-yl)-5-(3-carboxymethoxyphenyl)-2-(4-sulfophenyl)-2H-tetrazolium and phenylmethasulfazone](100:20) (Promega) were added to each well, plates were incubated for 3 h, and absorbance was determined at 490 nm. Viability was assessed on the basis of cellular conversion of MTS dye into a soluble formazan product using the Promega CellTiter 96 Aqueous Non-Radioactive Cell Proliferation Assay as described in Falzari K, Zhu Z, Pan D, Liu H, Hongmanee P, et al. (2005). In vitro and in vivo activities of macrolide derivatives against *Mycobacterium tuberculosis* were determined as described in Ekins, S, Reynolds, R C, Franzblau, S G, et al. Enhancing Hit Identification in *Mycobacterium tuberculosis* Drug Discovery Using Validated Dual-Event Bayesian Models PLOS ONE (2013) 8:5, e63240.

Cytotoxicity data from several mammalian cell lines including Vero (monkey kidney cells), HepG2 (human liver cells) and J774 (murine monocyte/macrophages) demonstrate that the lead berkeleylactone compounds have none or greatly diminished toxicity towards these cells (Table 14). The wide therapeutic index of DNA 76 between its efficacious concentration to induce bactericidal activity, ~1 µg/ml, and mammalian toxicity, ~60 µg/ml, demonstrates a good safety profile for these compounds. Additionally the BPL76 compound was tested against primary human peripheral blood mononuclear cells (PBMCs) and induced very little cell death, with only up to 60% death induced at the highest concentration tested, 500 µg/ml (not shown).

TABLE 14

Cytotoxicity Data of BPL compounds and known antibiotics.

|  | Stock (mg/ml) | Vero cell IC50 (ug/ml) | HepG2 IC50 (ug/ml) | J774 IC50 (ug/ml) |
|---|---|---|---|---|
| BPL 81 | 10 | 55.69 | >100 | 37.2 |
| BPL 84* | 10 | >100 | >100 | >100 |
| BPL 76 | 10 | 61.5 | 64.85 | 16.79 |
| BPL 76-Methyl ester | 10 | 74.05 | 55.64 | 38 |
| BPL 88 | 10 | >100 | >100 | 42.55 |
| BPL 94 | 10 | 43.77 | 85.16 | 40.69 |
| BPL 95 | 10 | 75.59 | >100 | 74.12 |
| RMP - Rifampicin | 10 | >100 | >100 | 95.82 |
| TMC207 | 1 | >10 | >10 | >10 |

The foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

We claim:

1. A compound of formula (I), or a pharmaceutically acceptable salt thereof,

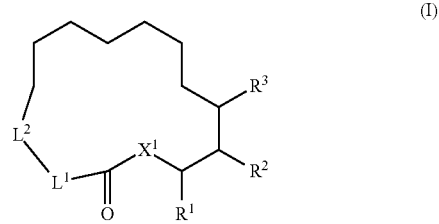

(I)

wherein $X^1$ is O or NH;

$R^1$ is $C_{1-4}$alkyl, $C_{1-4}$haloalkyl, $C_{1-3}$alkyleneOH, or —$C_{1-3}$alkylene-$OC_{1-4}$alkyl;

$R^2$ is hydrogen, OH, —$OC_{1-4}$alkyl, —$OC(O)C_{1-4}$alkyl, —$OC(O)C(CF_3)(OCH_3)Ph$, $NH_2$, —$NHC_{1-4}$alkyl, —$N(C_{1-4}alkyl)_2$, —$NHC(O)C_{1-4}$alkyl, —$N(C_{1-4}alkyl)C(O)C_{1-4}$alkyl, SH, —$SC_{1-4}$alkyl, or —$SC(O)C_{1-4}$alkyl;

$R^3$ is hydrogen, OH, —$OC_{1-4}$alkyl, —$OC(O)C_{1-4}$alkyl, $NH_2$, —$NHC_{1-4}$alkyl, —$N(C_{1-4}alkyl)_2$, —$NHC(O)C_{1-4}$alkyl, —$N(C_{1-4}alkyl)C(O)C_{1-4}$alkyl, SH, —$SC_{1-4}$alkyl, or —$SC(O)C_{1-4}$alkyl;

$L^1$ is

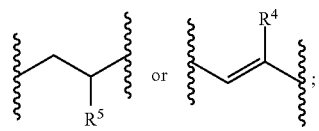

$R^4$ is hydrogen or methyl;

$R^5$ is —S—$CH_2$—$CH(R^7)$—$X^2$;

$R^7$ is hydrogen, $C_{1-4}$alkyl, OH, —$OC_{1-4}$alkyl, —$OC(O)C_{1-4}$alkyl, $NH_2$, —$NHC_{1-4}$alkyl, —$N(C_{1-4}alkyl)_2$, —$NHC(O)C_{1-4}$alkyl, —$N(C_{1-4}alkyl)C(O)C_{1-4}$alkyl, SH, —$SC_{1-4}$alkyl, or —$SC(O)C_{1-4}$alkyl;

$L^2$ is

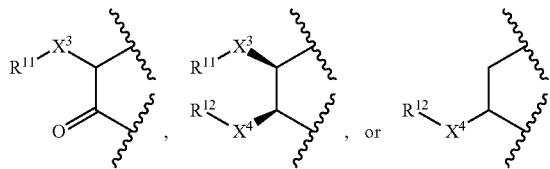

$X^3$ and $X^4$ are each independently O, S, NH, or $N(C_{1-4}alkyl)$;

$R^{11}$ is hydrogen, $C_{1-4}alkyl$, —$C(O)C_{1-4}alkyl$, —$C(O)C_{1-4}alkylene-X^5$, or —$C(O)C(CF_3)(OCH_3)Ph$;

$R^{12}$ is hydrogen, $C_{1-4}alkyl$, —$C(O)C_{1-4}alkyl$, —$C(O)C_{1-4}alkylene-X^6$, or —$C(O)C(CF_3)(OCH_3)Ph$; and $X^2$, $X^5$, and $X^6$ are independently a carboxylic acid, a carboxylic acid bioisostere, or a prodrug thereof;

provided that a) one of $R^2$ and $R^3$ is not hydrogen, or b) $L^1$ is

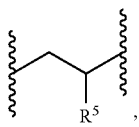

or c) $L^2$ is

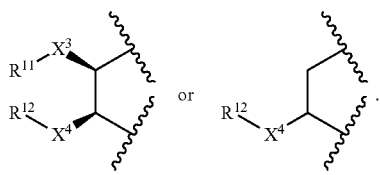

2. The compound of claim 1, or a pharmaceutically acceptable salt thereof, wherein $L^1$ is

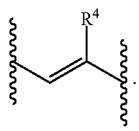

3. The compound of claim 1, or a pharmaceutically acceptable salt thereof, wherein $L^1$ is

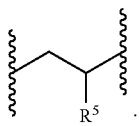

4. The compound of claim 1, or a pharmaceutically acceptable salt thereof, wherein $L^2$ is

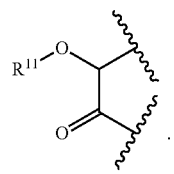

5. The compound of claim 1, or a pharmaceutically acceptable salt thereof, wherein $L^2$ is

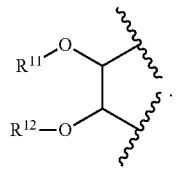

6. The compound of claim 1, or a pharmaceutically acceptable salt thereof, wherein $L^2$ is

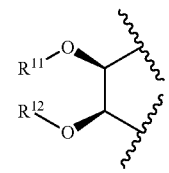

7. The compound of claim 1, or a pharmaceutically acceptable salt thereof, wherein $R^1$ is $C_{1-4}alkyl$ or —$C_{1-3}alkylene-OH$; and $R^2$ and $R^3$ are each hydrogen.

8. The compound of claim 1, or a pharmaceutically acceptable salt thereof, wherein $R^1$ is $C_{1-4}alkyl$; $R^2$ is hydrogen; and $R^3$ is OH, —$OC_{1-4}alkyl$, or —$OC(O)C_{1-4}alkyl$.

9. The compound of claim 1, or a pharmaceutically acceptable salt thereof, wherein $R^1$ is $C_{1-4}alkyl$; $R^2$ is OH, —$OC_{1-4}alkyl$, —$OC(O)C_{1-4}alkyl$, or —$OC(O)C(CF_3)(OCH_3)Ph$; and $R^3$ is hydrogen.

10. The compound of claim 1, or a pharmaceutically acceptable salt thereof, wherein $R^{11}$ is hydrogen, $CH_3$, —$C(O)CH_3$, —$C(O)CH_2CH_2-X^5$, or —$C(O)C(CF_3)(OCH_3)Ph$.

11. The compound of claim 1, or a pharmaceutically acceptable salt thereof, wherein $R^{11}$ is hydrogen, —$C(O)C_{1-4}alkyl$, —$C(O)C_{1-4}alkylene-X^5$, or —$C(O)C(CF_3)(OCH_3)Ph$; and $R^{12}$ is hydrogen, —$C(O)C_{1-4}alkyl$, or —$C(O)C(CF_3)(OCH_3)Ph$.

12. The compound of claim 1, or a pharmaceutically acceptable salt thereof, wherein $R^{11}$ is hydrogen, —$C(O)C_{1-4}alkyl$, or —$C(O)C(CF_3)(OCH_3)Ph$; and $R^{12}$ is hydrogen, —$C(O)C_{1-4}alkyl$, —$C(O)C_{1-4}alkylene-X^6$, or —$C(O)C(CF_3)(OCH_3)Ph$.

13. The compound of claim 1, or a pharmaceutically acceptable salt thereof, wherein $X^1$ is O.

14. The compound of claim 1, or a pharmaceutically acceptable salt thereof, wherein $X^1$ is NH.

15. The compound of claim 1 selected from the group consisting of:

(S)-2-hydroxy-3-(((3R,6S,16R)-6-hydroxy-16-methyl-2,5-dioxooxacyclohexadecan-3-yl)thio)propanoic acid;

4-(((3R,6S,16R)-3-(((S)-2-carboxy-2-hydroxyethyl)thio)-16-methyl-2,5-dioxooxacyclohexadecan-6-yl)oxy)-4-oxobutanoic acid;

4-(((6S,15S,16R,E)-15-hydroxy-16-methyl-2,5-dioxooxacyclohexadec-3-en-6-yl)oxy)-4-oxobutanoic acid;
4-(((6S,16R,E)-14-hydroxy-16-methyl-2,5-dioxooxacyclohexadec-3-en-6-yl)oxy)-4-oxobutanoic acid;
4-(((5R,6S,16R,E)-5-hydroxy-16-methyl-2-oxooxacyclohexadec-3-en-6-yl)oxy)-4-oxobutanoic acid;
(5R,6S,15S,16R,E)-5,6,15-trihydroxy-16-methyloxacyclohexadec-3-en-2-one;
4-(((5R,6S,15S,16R,E)-5,15-dihydroxy-16-methyl-2-oxooxacyclohexadec-3-en-6-yl)oxy)-4-oxobutanoic acid;
4-(((5R,6S,16S,E)-5-hydroxy-16-(hydroxymethyl)-2-oxooxacyclohexadec-3-en-6-yl)oxy)-4-oxobutanoic acid;
methyl (S)-2-hydroxy-3-(((3R,6S,16R)-6-hydroxy-16-methyl-2,5-dioxooxacyclohexadecan-3-yl)thio)propanoate;
methyl (S)-2-acetoxy-3-(((3R,6S,16R)-6-acetoxy-16-methyl-2,5-dioxooxacyclohexadecan-3-yl)thio)propanoate;
(2R,3S,12S,13R,E)-2-methyl-16-oxooxacyclohexadec-14-ene-3,12,13-triyl triacetate;
(2R,3S,12S,13R,E)-2-methyl-16-oxooxacyclohexadec-14-ene-3,12,13-triyl tris(3,3,3-trifluoro-2-methoxy-2-phenylpropanoate);
(5S,16R,E)-5-hydroxy-16-methyloxacyclohexadec-3-en-2-one;
(5R,6S,16R,E)-5,6-dihydroxy-16-methyloxacyclohexadec-3-en-2-one;
4-(((5R,6S,16R,E)-6-hydroxy-16-methyl-2-oxooxacyclohexadec-3-en-5-yl)oxy)-4-oxobutanoic acid; or
a pharmaceutically acceptable salt thereof.

16. A pharmaceutical composition comprising the compound of claim 1, or a pharmaceutically acceptable salt thereof, and a pharmaceutically acceptable carrier.

17. A method of treating a microbial infection comprising administering to a subject infected with a microbe a therapeutically effective amount of the compound of claim 1, or a pharmaceutically acceptable salt thereof.

18. A method of inhibiting microbial growth comprising contacting a microbe with a therapeutically effective amount of the compound of claim 1, or a pharmaceutically acceptable salt thereof.

19. A method of treating a yeast infection comprising administering, to a subject in need thereof, a therapeutically effective amount of the compound of claim 1, or a pharmaceutically acceptable salt thereof.

* * * * *